(12) United States Patent
Ben-Haim

(10) Patent No.: US 10,776,961 B2
(45) Date of Patent: Sep. 15, 2020

(54) REGISTERING NUCLEAR MEDICINE DATA

(71) Applicant: Navix International Limited, Tortola (VG)

(72) Inventor: Shlomo Ben-Haim, London (GB)

(73) Assignee: Navix International Limited, Road Town (VG)

( * ) Notice: Subject to any disclaimer, the term of this patent is extended or adjusted under 35 U.S.C. 154(b) by 631 days.

(21) Appl. No.: 15/500,189

(22) PCT Filed: Jul. 30, 2015

(86) PCT No.: PCT/IB2015/055772
§ 371 (c)(1),
(2) Date: Jan. 30, 2017

(87) PCT Pub. No.: WO2016/016839
PCT Pub. Date: Feb. 4, 2016

(65) Prior Publication Data
US 2017/0278280 A1 Sep. 28, 2017

Related U.S. Application Data

(60) Provisional application No. 62/030,750, filed on Jul. 30, 2014, provisional application No. 62/030,825, filed on Jul. 30, 2014.

(51) Int. Cl.
*A61B 6/00* (2006.01)
*G06T 11/00* (2006.01)
(Continued)

(52) U.S. Cl.
CPC ............ *G06T 11/006* (2013.01); *A61B 6/037* (2013.01); *A61B 6/12* (2013.01); *A61B 6/425* (2013.01);
(Continued)

(58) Field of Classification Search
CPC ... A61B 2090/3966; A61B 6/037; A61B 6/12; A61B 6/425; A61B 6/4258; A61B 6/487;
(Continued)

(56) References Cited

U.S. PATENT DOCUMENTS 5,077,035 A 12/1991 Wieland et al.
5,368,030 A 11/1994 Zinreich et al.
(Continued)

FOREIGN PATENT DOCUMENTS

CN 102056544 5/2011
CN 102120039 7/2011
(Continued)

OTHER PUBLICATIONS

Supplementary Partial European Search Report and the European Search Opinion dated Aug. 1, 2018 From the European Patent Office Re. Application No. 15827816.8. (8 Pages).
(Continued)

*Primary Examiner* — Amanda K Hulbert

(57) ABSTRACT

A method of data presentation in which NM data and x-ray data (or other structural and/or functional data sets) are combined for display. In some exemplary embodiments of the invention, the combination uses rules, for example Boolean rules to generate a display. In some exemplary embodiments of the invention, the combination uses a marker visible in the NM and x-ray modalities. Optionally, the marker includes a removable radioactive section.

35 Claims, 13 Drawing Sheets

(51) Int. Cl.
*A61B 6/03* (2006.01)
*A61B 90/00* (2016.01)
*A61B 6/12* (2006.01)

(52) U.S. Cl.
CPC ............ *A61B 6/4258* (2013.01); *A61B 6/503* (2013.01); *A61B 6/5205* (2013.01); *A61B 6/5235* (2013.01); *A61B 6/5294* (2013.01); *A61B 6/547* (2013.01); *A61B 90/39* (2016.02); *A61B 6/487* (2013.01); *A61B 6/5288* (2013.01); *A61B 6/541* (2013.01); *A61B 2090/3966* (2016.02); *G06T 2210/41* (2013.01)

(58) Field of Classification Search
CPC ..... A61B 6/503; A61B 6/5205; A61B 6/5235; A61B 6/5288; A61B 6/5294; A61B 6/541; A61B 6/547; A61B 90/39; G06T 11/006; G06T 2210/41
See application file for complete search history.

(56) References Cited

U.S. PATENT DOCUMENTS

| | | | |
|---|---|---|---|
| 5,789,420 | A | 8/1998 | Efange et al. |
| 6,211,360 | B1 | 4/2001 | Glick et al. |
| 6,358,492 | B1 | 3/2002 | Kuhar et al. |
| 6,511,500 | B1 | 1/2003 | Rahme |
| 6,845,267 | B2 | 1/2005 | Harrison et al. |
| 8,359,092 | B2 | 1/2013 | Hayam et al. |
| 8,364,285 | B2 | 1/2013 | Rezai |
| 9,265,590 | B2 * | 2/2016 | Zagorchev ............ A61B 6/508 |
| 2004/0054248 | A1 | 3/2004 | Kimchy et al. |
| 2004/0138550 | A1 | 7/2004 | Hartlep et al. |
| 2004/0152975 | A1 | 8/2004 | Blevis |
| 2005/0008126 | A1 | 1/2005 | Juh et al. |
| 2005/0261672 | A1 | 11/2005 | Deem et al. |
| 2006/0127309 | A1 | 6/2006 | Raffel et al. |
| 2006/0287648 | A1 | 12/2006 | Schwartz |
| 2008/0230705 | A1 | 9/2008 | Rousso et al. |
| 2009/0292157 | A1 | 11/2009 | Bruce et al. |
| 2010/0221182 | A1 | 9/2010 | Purohit et al. |
| 2011/0105896 | A1 * | 5/2011 | Zagorchev ............ A61B 6/508 600/426 |
| 2011/0189096 | A1 | 8/2011 | Watanabe et al. |
| 2011/0218818 | A1 | 9/2011 | Butson et al. |
| 2011/0238128 | A1 | 9/2011 | Dobak, III |
| 2012/0065492 | A1 | 3/2012 | Gertner et al. |
| 2012/0155733 | A1 | 6/2012 | Wagenknecht |
| 2012/0271171 | A1 | 10/2012 | Gertner |
| 2013/0123773 | A1 | 5/2013 | Schwartz |
| 2013/0267829 | A1 | 10/2013 | Ojha et al. |
| 2017/0263021 | A1 | 9/2017 | Ben-Haim |

FOREIGN PATENT DOCUMENTS

| | | |
|---|---|---|
| EP | 1733692 | 12/2006 |
| EP | 2474526 | 7/2012 |
| JP | 2007-236837 | 9/2007 |
| JP | 2007236837 | 9/2007 |
| KR | 20090074399 | 7/2009 |
| WO | WO 01/82978 | 11/2001 |
| WO | WO 02/102238 | 12/2002 |
| WO | WO 2009/150564 | 12/2009 |
| WO | WO 2011/091069 | 7/2011 |
| WO | WO 2013/038011 | 3/2013 |
| WO | WO 2014/115148 | 7/2014 |
| WO | WO 2014/115150 | 7/2014 |
| WO | WO 2014/115151 | 7/2014 |
| WO | WO 2014/115152 | 7/2014 |
| WO | WO 2014/141247 | 9/2014 |
| WO | WO 2015/033317 | 3/2015 |
| WO | WO 2015/033319 | 3/2015 |
| WO | WO 2015/104672 | 7/2015 |
| WO | WO 2016/016837 | 2/2016 |
| WO | WO 2016/016839 | 2/2016 |

OTHER PUBLICATIONS

International Preliminary Report on Patentability dated Feb. 9, 2017 From the International Bureau of WIPO Re. Application No. PCT/IB2015/055772. (6 Pages).
International Search Report and the Written Opinion dated Jun. 5, 2014 From the International Searching Authority Re. Application No. PCT/IL2014/050086.
International Search Report and the Written Opinion dated Jun. 9, 2014 From the International Searching Authority Re. Application No. PCT/IL2014/050088.
International Search Report and the Written Opinion dated Jun. 10, 2014 From the International Searching Authority Re. Application No. PCT/IL2014/050089.
International Search Report and the Written Opinion dated May 15, 2014 From the International Searching Authority Re. Application No. PCT/IL2014/050090.
International Search Report and the Written Opinion dated Nov. 27, 2015 From the International Searching Authority Re. Application No. PCT/IB2015/055767.
International Search Report and the Written Opinion dated Jul. 28, 2014 From the International Searching Authority Re. Application No. PCT/IL2014/050246.
International Search Report and the Written Opinion dated Nov. 30, 2015 From the International Searching Authority Re. Application No. PCT/IB2015/055772.
Invitation to Pay Additional Fees dated Apr. 10, 2014 From the International Searching Authority Re. Application No. PCT/IL2014/050090.
Arora "Recent Insights Into the Role of the Autonomic Nervous System in the Creation of Substrate for Atrial Fibrillation—Implications for Therapies Targeting the Atrial Autonomic Nervous System", Circulation: Arrhythmia and Electrophysiology, XP055236980, 5(4): 850-859, Aug. 1, 2012. p. 6, 7, Chapter 'Recent Developments in Imaging of the Autonomic Innervation of the Atria—Implications for AF Ablation'.
Arora et al. "Porcine Intrinsic Cardiac Ganglia", The Anatomical Record Part A, 271A: 249-258, 2003.
Burnstock "Autonomic Neurotransmission: 60 Years Since Sir Henry Dale", The Annual Review of Pharmacology and Toxicology, 49: 1-30, 2009.
Esler et al. "Sympathetic Nerve Activity and Neurotransmitter Release in Humans: Translation From Pathophysiology Into Clinical Practice", Acta Physiologica Scandinavica, 177: 275-284, 2003.
Hirsch et al. "Measuring Activity of the Autonomic Nervous System in Humans", Obesity Research, 11(1): 2-4, Jan. 2003.
IAEA "Technetium-99m Radiopharmaceuticals: Status and Trends", IAEA, International Atomic Energy Agency Radioisotopes and Radiopharmaceuticals Series, 1: 1-378, 2009.
Knuepfer et al. "Direct Assessment of Organ Specific Sympathetic Nervous System Activity in Normal and Cardiovascular Disease States", Experimental Physiology, 95(1): 32-33, 2010.
Kosa et al. "Principles and Methods of Myocardial Perfusion Imaging", Chap.2: 33-57.
Langer et al. "PET and SPET Tracers for Mapping the Cardiac Nervous System", European Journal of Nuclear Medicine and Molecular Imaging, 29(3): 416-434, Mar. 2002.
Linz et al. "Atrial Autonomic Innervation: A Target for Interventional Antiarrhythmic Therapy?", Journal of the American College of Cardiology, JACC, p. 1-33, 2013.
Malliani et al. "Emerging Excitatory Role of Cardiovascular Sympathetic Afferents in Pathophysiological Conditions", Hypertension, 39: 63-68, Jan. 2002.
Malpas "Sympathetic Nervous System Overactivity and Its Role in the Development of Cardiovascular Disease", Physiology Review, 90: 513-557, 2010.
Matsunari et al. "Iodine-123 Metaiodobenzylguanidinen Imaging and Carbon-11 Hydroxyephedrine Positron Emission Tomography Compared in Patients With Left Ventricular Dysfunction", Circulation Cardiovascular Imaging, 3: 595-603, Sep. 2010.

(56) References Cited

OTHER PUBLICATIONS

Mourot et al. "Effects of the Cold Pressor Test on Cardiac Autonomic Control in Normal Subjects", Physiology Research, 58: 83-91, 2009.
Rispler et al. "Quantitative 123I-MIBG SPECT/CT Assessment of Cardiac Sympathetic Innervation—A New Diagnostic Tool for Heart Failure", International Journal of Cardiology, XP028740607, 168(2): 1556-1558, Jan. 17, 2013. p. 1556, col. 1-p. 1558, col. 1.
Ross et al. "Research Applications of Selected [123]I-Labeled Neuroreceptor SPECT Imaging Ligands", Journal of Nucelar Medicine and Technology, 32(4): 209-214, Dec. 2004.
Sen "Some Observations of Decapsulation and Denervation of the Kidney", The British Journal of Urology, 8(4): 319-328, 1936.
Singh "Chemistry, Design, and Structure-Activity Relationship of Cocaine Antagonists", Chemical Reviews, 100: 925-1024, 2000.
Sisson et al. "Metaiodobenzylguanidine to Map Scintigraphically the Adrenergic Nervous System in Man", The Journal of Nuclear Medicine, 28(10): 1625-1636, Oct. 1987.
Smith "Extrinsic Inputs to Intrinsic Neurons in the Porcine Heart In Vitro", The American Journal of Physiology, 276(2/Pt.2): R455-R467, Feb. 1999.
Smith et al. "Simulation of Cardiovascular System Diseases by Including the Autonomic Nervous System Into a Minimal Model", Computer Methods and Programs in Biomedicine, 86(2): 153-160, May 2007.
Tan et al. "Autonomic Nerves in Pulmonary Veins", Heart Rythm, 4(3 Suppl.): S57-S60, Mar. 2007.
Travin "Cardiac Autonomic Imaging With SPECT Tracers", Journal of Nuclear Cardiology, 20(1): 128-143, Feb. 2013.
Troisi et al. "Relation of Obesity and Diet Sympathetic Nervous System Activity", Hypertension, 17(5): 669-677, May 1991.
Vallabhajosula et al. "Radioiodinated Metaiodobenzylguanidine (MIBG): Radiochemistry, Biology, and Pharmacology", Seminars in Nuclear Medicine, 41: 324-333, 2011.
Vissing et al. "Stimulation of Skin Sympathetic Nerve Discharge by Central Command", Circulation Research, 69(1): 228-238, Jul. 1991.
Wong et al. "Pericardial Fat Is Associated With Atrial Fibrillation Severity and Ablation Outcome", Journal of the American College of Cardiology, JACC, 57(17): 1745-1751, 2011.
Zhang et al. "The Celiac Ganglia: Anatomic Study Using MRI in Cadavers", American Journal of Roentgenology, AJR, 186(6): 1520-1523, Jun. 2006.
Communication Pursuant to Article 94(3) EPC dated Jan. 7, 2020 From the European Patent Office Re. Application No. 15827816.8. (4 Pages).
Translation of Notification dated Sep. 18, 2019 From OA dated Aug. 26, 2019 From the State Intellectual Property Office of the People's Republic of China Re. Application No. 2015800016695.

* cited by examiner

REGISTERING NUCLEAR MEDICINE DATA

RELATED APPLICATIONS

This application is a National Phase of PCT Patent Application No. PCT/IB2015/055772, having International filing date of Jul. 30, 2015, which claims the benefit of priority under 35 USC § 119(e) of U.S. Provisional Patent Application Nos. 62/030,750 and 62/030,825, both filed on Jul. 30, 2014.

PCT Patent Application No. PCT/IB2015/055772 is also related to:

PCT Patent Application No. PCT/IL2014/050086 filed Jan. 24, 2014,

PCT Patent Application No. PCT/IL2014/050088 filed Jan. 24, 2014,

PCT Patent Application No. PCT/IL2014/050089 filed Jan. 24, 2014,

PCT Patent Application No. PCT/IL2014/050090 filed Jan. 24, 2014,

PCT Patent Application No. PCT/IL2014/050246 filed Mar. 11, 2014; and

PCT applications and publications PCT/IB2015/053984 (filed on May 27, 2015); WO2015/104672; WO2015/033319 and WO2015/033317.

The contents of the above applications are all incorporated by reference as if fully set forth herein in their entirety.

FIELD AND BACKGROUND OF THE INVENTION

The present invention, in some embodiments thereof, relates to registering nuclear medicine data, for example, images, for example for use of the data during a fluoroscopy based procedure.

SUMMARY OF THE INVENTION

There is provided in accordance with some exemplary embodiments of the invention, a method of data presentation, comprising:

acquiring functional data in registration with at least one anatomical indicator at a first time and location;

acquiring a position of said at least one anatomical indicator at a second time and location; and displaying at least an indication of said functional data registered to said acquired position. Optionally, said acquiring functional data comprises acquiring NM (nuclear medicine) data in conjunction with the acquisition of at least one radio-opaque marker. Optionally or alternatively, said acquiring functional data comprises acquiring data in conjunction with a position determination using a position sensor. Optionally or alternatively, said acquiring functional data comprises resolving a multi-point image of a radioactive fiduciary marker. Optionally or alternatively, said acquiring functional data comprises resolving an asymmetric property of a radioactive fiduciary marker. Optionally or alternatively, said anatomical indicator comprises a radioactive fiduciary marking which is co-located with a radio-opaque marking. Optionally, the method comprises removing said radioactive fiduciary marking between said first time and said second time.

In some exemplary embodiments of the invention, said acquiring a position comprises acquiring a 2D position.

In some exemplary embodiments of the invention, said acquiring a position comprises acquiring a planar x-ray image. Optionally, said displaying comprises overlaying at least part of said functional data over said x-ray image. Optionally or alternatively, said acquiring functional data comprises acquiring a plurality of positions of said anatomical indicator, with said functional data acquisition. Optionally or alternatively, the method comprises analyzing said displaying to identify one or more lesions on said planar x-ray image.

There is provided in accordance with some exemplary embodiments of the invention, a method of image data registration, comprising:

(a) collecting first image data in registration to at least a first marker, said collecting including acquisition over a plurality of positions of said first marker;

(b) collecting second image data of a different modality from said first image data including a position of said first marker; and (c) registering said first image data to said second image data based on a registration of said position of said first marker to said plurality of positions of said first marker. Optionally, said image data comprises continuously acquired image data. Optionally, said image data and said positions are collected over at least one whole entire cardiac cycle. Optionally or alternatively, the method comprises processing said plurality of positions into a model of a position of said first marker.

In some exemplary embodiments of the invention, said collecting second image data comprises collecting one or more planar x-ray images. Optionally, said collecting second image data comprises extracting said position of said first marker from said planar x-ray image.

In some exemplary embodiments of the invention, said registering comprises using said plurality of positions to constrain a range of possible registrations.

There is provided in accordance with some exemplary embodiments of the invention, apparatus for image display, comprising:

(a) a memory having stored thereon NM data and a position of at least one anatomical location;

(b) an input for x-ray images;

(c) a position extractor which extracts a position of a fiduciary marker from an image received through said input; and (d) overlay circuitry which registers said extracted position to said anatomical location and overlays an indication of said NM data on said inputted image.

Optionally, said position extractor also extracts the position of at least one tool and said overlay circuitry overlays said tool position on said image. Optionally or alternatively, said position extractor includes a recognizer which recognizes a fiduciary marker on the image.

There is provided in accordance with some exemplary embodiments of the invention, a fiduciary marker comprising:

(a) a radio-opaque section; and (b) a radioactive marking section comprising a mounting for a removable radio-active marker portion. Optionally, said mounting comprises a receptacle for a radioactive fluid. Optionally or alternatively, said mounting comprises a receptacle for a radioactive insert. Optionally or alternatively, said mounting comprises an interference based fitting.

In some exemplary embodiments of the invention, said radioactive marking section has a center activity of radiation co-located in at least two dimensions with a center of opacity of said radio-opaque section.

In some exemplary embodiments of the invention, at least one of said sections is ring-shaped.

In some exemplary embodiments of the invention, the marker comprises an adhesive layer with adhesive suitable for long-term adhesion to a human skin.

In some exemplary embodiments of the invention, the marker comprises a radioactive marking portion mounted in said mounting. Optionally, an energy signature of said radioactive portion includes a plurality of distinct energy bands. Optionally, at least one of said energy bands is not associated with an energy signature of a biocompatible tracer in clinical use. Optionally or alternatively, said radioactive marker portion is formed of a non-bio-compatible radioactive material.

There is provided in accordance with some exemplary embodiments of the invention, a fiduciary marker comprising:

(a) a radio-opaque section defining at least one point for identification in an x-ray image; and (b) a radioactive section defining at least one point for identification in a NM image, wherein said two points are co-located and overlap in at least two dimensions. Optionally, at least one of said points is defined by a point portion. Optionally or alternatively, at least one of said points is defined by a ring portion. Optionally or alternatively, said radioactive section includes a removable radioactive marking portion. Optionally or alternatively, the marker comprises an adhesive layer with adhesive suitable for long-term adhesion to a human skin.

There is provided in accordance with some exemplary embodiments of the invention, a fiduciary marker comprising:

(a) a radio-opaque section defining at least one point for identification in an x-ray image; and (b) a radioactive section defining at least one point for identification in a NM image, wherein said radioactive section has a center of activity unaligned with said radio-opaque point, in at least two dimensions. Optionally, said radioactive section is asymmetric. Optionally or alternatively, said asymmetry is in geometry. Optionally or alternatively, said asymmetry is in radioactive material distribution.

There is provided in accordance with some exemplary embodiments of the invention, a method of using a fiduciary marker, comprising:

(a) attaching a fiduciary marker to a patient;

(b) imaging the patient using an NM system to obtain NM data;

(c) determining a location of said fiduciary marker on said patient after said imaging; and (d) generating a dataset including an NM image and a position of said fiduciary marker, from said NM data and said determined location. Optionally, said fiduciary marker is radio-opaque and comprising using a position sensor for said determining. Optionally or alternatively, said fiduciary marker is radioactive. Optionally or alternatively, the method comprises attaching said fiduciary marker to a patient and thereafter making said marker radioactive. Optionally or alternatively, the method comprises making said marker non-radioactive to less than 10% of a pervious radioactivity without removing it from a patient and over a period of less than 10 minutes. Optionally or alternatively, determining a location comprises identifying said marker in said imaged NM data. Optionally, determining a location comprises identifying an energy signature of said marker.

In some exemplary embodiments of the invention, determining a location comprises identifying a shape of said marker.

In some exemplary embodiments of the invention, attaching comprises attaching to a skin.

In some exemplary embodiments of the invention, attaching comprises intrabody insertion.

In some exemplary embodiments of the invention, said generating comprises generating at a location remote from said imaging.

There is provided in accordance with some exemplary embodiments of the invention, a NM data processor, comprising:

(a) an input for NM data;

(b) an image reconstructer; and (c) a fiduciary marker extractor. Optionally, said extractor is configured to identify said marker at a point other than a center of radioactive activity thereof.

There is provided in accordance with some exemplary embodiments of the invention, a method of displaying data from multiple data sets, comprising:

(a) providing a rule including one or more first properties for a first data set; one or more second properties for a second data set; and a relationship between the first and second properties;

(b) applying said rule to a first data set;

(b) applying said rule to a second data set; and (c) displaying an indication based on said relationship of said rule as applied to a result of said applying in (a) and (b). Optionally, said first and second data sets are of different modalities. Optionally or alternatively, said relationship relates structural features in one data set with functional features in another data set. Optionally or alternatively, said displaying is binary, showing an indication if the rule matches and not showing an indication if the rule does not match. Optionally or alternatively, said indication comprises a portion of data from at least one of said data sets. Optionally or alternatively, said (b) applying comprises segmenting said first data set for application of said rule to one or more segments thereof. Optionally or alternatively, said first data set is NM and said second data set is x-ray. Optionally or alternatively, the method comprises building said rule form a first rule relating to said first data set and from a second rule relating to said second data set.

There is provided in accordance with some exemplary embodiments of the invention, a method of data presentation, comprising:

acquiring first data in registration with at least one anatomical indicator at a first time and location;

acquiring a position of said at least one anatomical indicator at a second time and location using x-ray imaging; and displaying at least an indication of said first data registered to said acquired position. Optionally, said acquiring first data comprises acquiring RF data.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon. Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as image processing, sensor analysis and/or database retrieval, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL
VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DESCRIPTION OF SPECIFIC EMBODIMENTS OF THE INVENTION

Figure 1A:
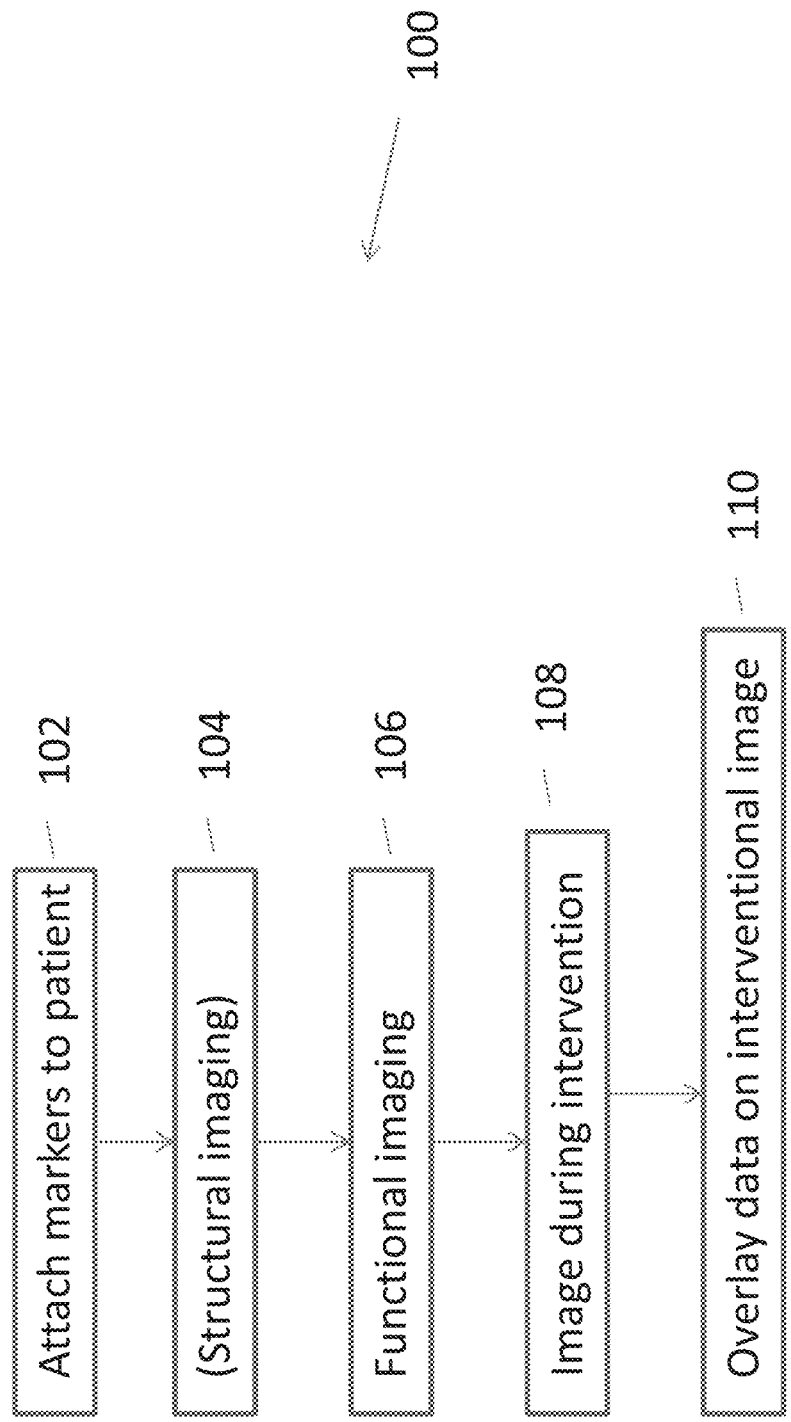
FIG. 1A is a flowchart of a method of imaging and intrabody navigation, in accordance with some exemplary embodiments of the invention.

The present invention, in some embodiments thereof, relates to registering nuclear medicine data, for example, images, for example for use of the data during a fluoroscopy based procedure.

An aspect of some embodiments of the invention relates to position determination on nuclear medicine ('NM') data. In some exemplary embodiments of the invention, the NM data is acquired with a fiduciary marker so that the NM data includes an anatomical position indication and the NM data is optionally reconstructed to provide an image. In some exemplary embodiments of the invention, this same fiduciary marker remains on/in the body and is used for (also) aligning a different (non-NM) imaging modality, such as CT or x-ray.

In exemplary embodiments of the invention, during a medical procedure, x-ray data, such as: planar x-ray images (or images of another imaging modality) of the patient including the fiduciary marker are acquired and the location of the fiduciary marker is extracted from the image(s). The location of the fiduciary marker in the planar x-ray image(s) is optionally aligned with the location in the NM data. The NM data itself or an indication thereof, such as a processed version thereof is then optionally overlaid on the x-ray images and/or otherwise integrated with the x-ray data. Optionally or alternatively, the x-ray data is used to indicate a relative position of (a) a tool and (b) an area that the NM data indicates is to be treated.

In some exemplary embodiments of the invention, the NM data is acquired during movement. Indication of one or more fiduciary marker may be acquired at a plurality of positions, which positions are aligned to the x-ray image.

An aspect of some embodiments of the invention relates to a method of data registration in which NM data is acquired using a fiduciary marker which may generate a plurality of position indications (e.g., due to natural motion thereof). In exemplary embodiments of the invention, this plurality of position indications is aligned with a single location provided by a different modality, such as the same fiduciary marker as imaged in x-ray. Optionally, the plurality of position indications is processed to generate a centroid. Optionally or alternatively, the plurality of position indications is processed to generate a cyclic position. Optionally, this cyclic position is matched to a change in position of said single location. For example, the plurality of position indications may indicate a range of positions a heart chamber may achieve and a correct one is correlated with a single indication provided by x-ray for the heart chamber.

Optionally or alternatively, the plurality of position indications is processed to provide an indication of expected error, e.g., to provide error signal (which is typically a signal indicating movement of body tissue). Such an error signal is optionally used when correlating two data sets (e.g., NM data and x-ray data). In some exemplary embodiments of the invention, the plurality of position indications are processed to generate movement information, which movement information is optionally used to select a point in the cycle (e.g., beginning of expiration or end of inspiration) and/or optionally track the movement of a marker (or location registered to the marker) over the entire or part of the cycle. Optionally, the data set at one point in the cycle (e.g., x-ray) is morphed to the data set in another point of the cycle based on the deformation of a model of the data set in the NM data. Optionally, the time in the cycle is determined based on the relative position between the markers as indicated in the x-ray data and which best correlates with a relative position of the markers in the NM data. Optionally, the time in the cycle is determined as being the time associated with the marker positions best correlated with the x-ray data (e.g., when analyzed as an image).

An aspect of some embodiments of the invention relates to circuitry that can be attached to existing x-ray systems, which circuitry receives x-ray image data and aligns the data with previously acquired and/or generated data, optionally 3D, of a different modality, optionally a functional modality, (e.g., MRI, PET, SPECT, ultrasound and/or RF data) and that includes one or more indication of a fiduciary marker. In some exemplary embodiments of the invention, a functional modality provides information re the functioning of tissue, for example, metabolic rate, blood flow, regional chemical composition and/or uptake. Such a modality may lack resolution and/or content to show anatomy.

In some exemplary embodiments of the invention, the circuitry extracts the position of one or more fiduciary markers from the x-ray image and/or other x-ray acquired data and aligns these positions with the indications of a fiduciary marker associated with the previously acquired/generated data.

In some exemplary embodiments of the invention, the previously acquired/generated data is NM data acquired using a fiduciary marker which is used for both NM and x-ray imaging. The fiduciary marker's anatomical location is optionally stable over time and imaging modalities.

An aspect of some embodiments of the invention relates to a fiduciary marker suitable for both x-ray imaging and a functional imaging modality, for example a 3D imaging modality, such as a NM imaging modality, such as PET or SPECT. In some exemplary embodiments of the invention, the marker includes a removable radioactive section, which may allow the marker to act as a NM marker. Optionally, the removable radioactive section is provided in a fluid containing capsule or is in the form of such a capsule. Optionally, the removable radioactive section is co-located and/or co-centered with a radio-opaque section, which may allow the marker to act as an x-ray marker.

In some exemplary embodiments of the invention, the radio-opaque (e.g., x-ray) and radio-active (e.g., NM) sections are co-centered in 1D, 2D or 3D. In one example, one of the sections is annular and the other section is at a center of the one section. In another example, one section is cross-shaped and the other section is annular and/or at the center of the one section.

In some exemplary embodiments of the invention, the radio-active section is not symmetric with respect to the radio-opaque section at least in one dimension. By symmetric, is meant the function (e.g., radiation emission and/or absorption), not size or shape. Such asymmetry may be used to ensure that appropriate software for extracting the NM section is used, which software includes the ability to identify the asymmetry. This is in contrast to software which simply picks a center of gravity of the emissions. Optionally, the asymmetry is used for orientation calculation.

In an exemplary embodiment of the invention, the NM sections is replaced by or augmented with a section imagable using a different modality such as ultrasound, MRI or RF.

An aspect of some embodiments of the invention relates to a fiduciary marker including radio opaque section and an aligned radio-lucent section (e.g., with an absorption along a radiation ray direction of less than 50%, 30%, 20%, 10% or intermediate percentages of the radio-opaque section) which provides contrast using a different imaging modality such as NM or RF. In some exemplary embodiments of the invention, a dielectric material is used for RF contrast and is co-centered in 1D, 2D or 3D with the center of a radio-opaque (e.g., x-ray) section. In some exemplary embodiments of the invention, the designs described herein for radio-active markers are used, except that the RF marking material is conductive or dielectric (as need may be). Optionally, a different design, with fixed radio-opaque and fixed dielectric sections is used (e.g., without the various connectors described herein and/or using a single housing for both radio-opaque and dielectric and/or using radio-opaque as a housing for dielectric or vice versa). Optionally or alternatively, radio-opaque material is embedded (e.g., as a powder) in a suitable dielectric material.

In some exemplary embodiment of the invention, the material for dielectric marking is chosen to have a dielectric constant which is significantly different from that of body tissues at the frequencies used for imaging. For example, the dielectric constant may be a factor of 1.5, 2, 5, 10, 30 or more or intermediate multiples of the dielectric constant of blood. In some embodiments, an RF marker comprises a reflector or a circuit, for example a circuit with non-linear response and/or which generates a second frequency in response to impinging of RF energy at a first frequency. It is noted that RF imaging may use various frequencies and various non-optical frequencies may be used as well, for example, 1-1000 Hz, 1-1000 KHz, 1-1000 MHz, 1-1000 GHz, 1-1000 THz, or lower and/or higher frequencies.

An aspect of some embodiments of the invention relates to data combining of two data sets, for example, NM data and x-ray data.

In an exemplary embodiment of the invention, when displaying the combined data one or more rules are applied. In some exemplary embodiments of the invention, the rules define properties on each of the data sets, (optionally different) and define the relationship between the properties to be used in deciding what to display. For example, a rule may be to show blotches of a certain size range in one data set only if the blotches have a position property with respect to an anatomy represented by the other data set. This may be done by processing and analyzing images, rather than pre-image data.

In some exemplary embodiments of the invention, the display is Boolean, in that features are either shown or not, depending on rule matching.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Navigation and/or Data Fusion Method

FIG. 1A is a flowchart 100 of a method of imaging and/or intrabody navigation, in accordance with an exemplary embodiment of the invention.

At 102, one or more markers are attached to a patient, for example, between 1 and 4 markers (or more), for example, 2 or 3. Optionally, the markers are attached to the body surface. Optionally or alternatively, the markers are attached to bone, for example, using screws. Optionally or alternatively, at least one marker is subcutaneous, optionally implanted using a needle or a catheter or other intrabody tool such as an endoscope.

In an exemplary embodiment of the invention, these markers can be detected both during functional imaging and during structural imaging and/or are modifiable (e.g., as described below) to be suitable for functional and structural imaging, as desired.

In an exemplary embodiment of the invention, the markers are placed at locations which are not expected to move relative to the body (e.g., spine). Optionally or alternatively, at least one marker is located where tissue movement is expected, whether attached to hard tissue (e.g., ribs) or soft tissue (e.g., abdominal fascia).

At 104, structural imaging is optionally carried out, also imaging the markers. In an exemplary embodiment of the invention, the structural imaging is 3D imaging, such as CT imaging or MRI imaging. Alternatively, the imaging is 2D imaging, for example, x-ray fluoroscopic imaging.

At 106, functional imaging is optionally carried out, also imaging the markers. In an exemplary embodiment of the invention, the functional imaging is MRI imaging or NM (nuclear medicine) imaging, such as SPECT or PET. In some embodiments imaging which may not be pure functional imaging is used, for example, RF based imaging, for example, as described in U.S. Pat. No. 6,885,191, the disclosure of which is incorporated herein by reference.

In some embodiments, for example for brain treatment (e.g., with a catheter) where less movement may be expected, structural imaging, such as CT imaging is carried out ahead of time and NM imaging is applied during or before the procedure. Optionally, a position sensing system is used to show a catheter location overlaid on the image(s). Optionally or alternatively, the catheter includes a radioactive marker identifiable in the NM image.

At 108, during an intervention, the patient and his fiduciary markers are imaged. In an exemplary embodiment of the invention, the imaging is fluoroscopic x-ray imaging using a catheter based intervention. At 110 the fiduciary markers detected at 108 are aligned with those detected at 104 and/or 106, so that data acquired at 104 and/or 106/can be overlaid on an image acquired at 108. Exemplary methods of alignment are described below. Optionally, once fiduciary markers are aligned, one or more anatomical indications in the images are aligned as well, for example, to improve the alignment. It is noted that in some cases the data sets aligned are of different dimensionality (e.g., each may be 2D, 2D+time, 3D, 3D+time, 4D or of a higher dimension).

In an exemplary embodiment of the invention, the displaying of 110 comprises selecting portion of each of the acquired images and/or related data to display, for example, as described below. Optionally or alternatively, to displaying, a thus combined data set is used for automatic processing, for example, for identifying progression of a tumor.

Some particular pairing of images in accordance with exemplary embodiments of the invention includes x-ray fluoroscopy together with functional MRI, NM, ultrasound. In an exemplary embodiment of the invention, at least some of the imaging methods use contrast material. Optionally, when two images are combined the effects of two different types of contrast material are thus displayable.

Exemplary Details and Variations on Navigation Methods

Figure 1B:
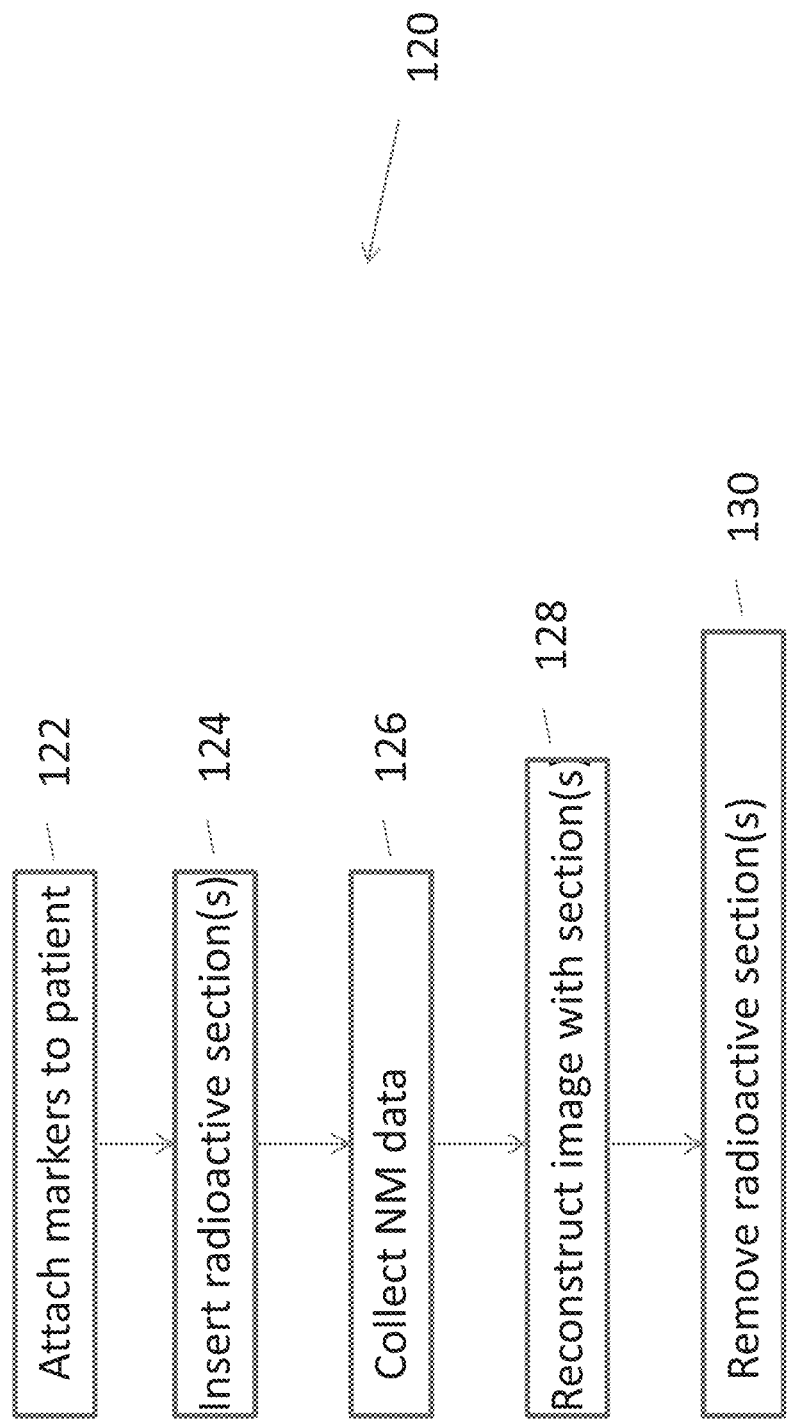
FIG. 1B is a flowchart of a method of nuclear medicine imaging for later navigation, in accordance with some exemplary embodiments of the invention.

FIG. 1B is a flowchart 122 of a method of nuclear medicine imaging for later navigation, in accordance with an exemplary embodiment of the invention.

At 122 one or more markers are attached to a patient. In some exemplary embodiments of the invention, attachment locations are selected such that they are located at different locations within the body to enable reconstruction of at least one or two dimension information of the surface they are attached to. Optionally or alternatively, markers are located where they are less likely to obstruct the view of the organs to be studied (e.g., for one or both imaging modalities). Optionally, markers are positioned so that when x-ray imaging during a procedure on an organ, with known and/or expected imager orientations/viewing directions, markers are near the region of interest (in the projection image) but do not block critical parts of the organ under study/treatment and/or important landmarks for navigation thereto. Optionally or alternatively, marker locations are selected so that the imager can be moved to avoid the markers blocking an important part of the image, while still providing a usable image.

At 124, the markers are made into radioactive markers, for example, by inserting radioactive sections into the markers or attaching such sections thereto. It is noted that the attaching of fiduciary markers may be carried out in one location and time, while actual imaging may be at an unknown delay. During such a delay, not only will any radioactive material decay, its radiation will also affect the patients and/or their surroundings. In an exemplary embodiment of the invention, the markers are designed (e.g., as described below) to allow radioactive portions to be added and/or removed, as desired, for example, as solid elements or as fluids.

In an exemplary embodiment of the invention, radioactive portions are attached/inserted just before imaging and are optionally removed thereafter. In an exemplary embodiment of the invention, the radioactive portions are attached by first removing a radio-opaque portion (e.g., a capsule with a groove that interlocks with a ridge in a recess of the marker) and replacing it with a radioactive portion. For example, a radio-opaque ball may be replaced by a radioactive ball, which ball is held by a plastic portion of the marker.

At 126, radioactive emission data is collected. Optionally, the patient moves (as a whole or in parts) during such collection. Optionally, the radio-opaque markers are used to align data from one position of the patient with data from another position of the patient. In some embodiments the fact and/or amount of patient motion is extracted from the change in position of anatomical parts of the image, for example, the spine and/or ribs. Optionally or alternatively, the movement of a marker within a single imaging session is tracked and used to determine a range of positions for the marker. Optionally, the positions of the marker are associated with different data, thus providing an image including time information (or binning or gating, as desired) for the collected emission data. This time information may be used during image reconstruction and/or data overlap.

In an exemplary embodiment of the invention, the radioactive emissions of the marker are at a different energy (e.g., different by 10%, 30%, 50% or intermediate or greater differences) from those of a tracer (e.g., I-123 or Tc-99) used on the patient, so they can be easily separated by the imaging system.

At 128 an image is optionally reconstructed form the collected data. Optionally, the image includes the image of the markers. Optionally or alternatively, the image of the markers is replaced by an indication of their position. Optionally, marker positions are replaced by a position distribution.

At 130 the radioactive materials are optionally removed from the markers. Optionally, the markers themselves stay attached to and/or in the body.

Figure 1C:
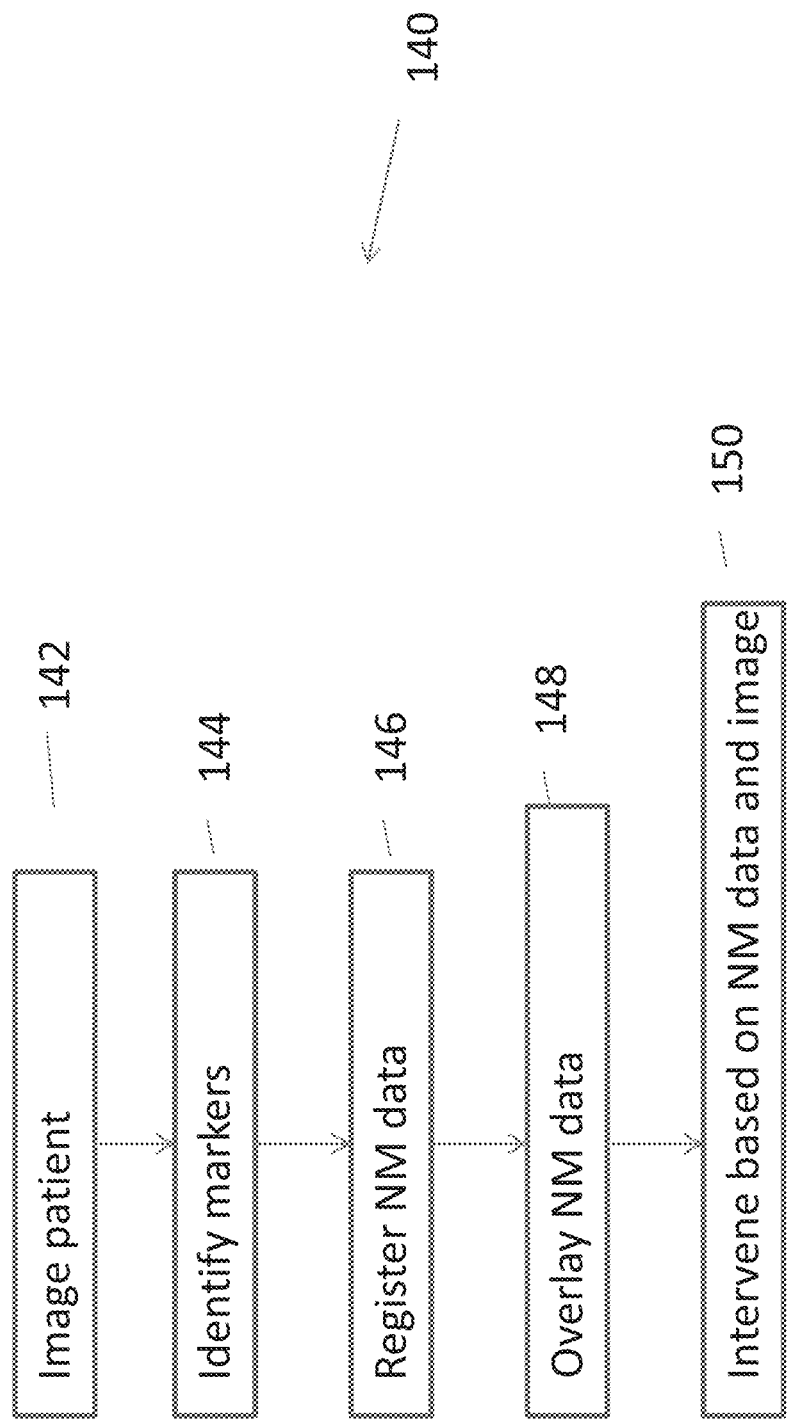
FIG. 1C is a flowchart of a method of intrabody navigation using nuclear medicine data, in accordance with exemplary embodiments of the invention.

FIG. 1C is a flowchart 140 of a method of intrabody navigation using nuclear medicine data, in accordance with an exemplary embodiment of the invention.

At 142 the patient is imaged, for example, using fluoroscopy. Such imaging can be, for example, as part of a catheter-based procedure or other procedure carried out under imaging. In some embodiments, the imaging is carried out before the procedure and further imaging is optionally not provided, or provided infrequently for example on a schedule (e.g., every 5, 15, 35 or intermediate or greater time periods), as needed or by request, during an intervention. Optionally, need is determined based on a progress of the procedure and/or position of the catheter.

In some exemplary embodiments of the invention, the patient is moved between 126 and 142 (e.g., between imaging/treatment rooms) and/or some time may pass, for example, 1-100 seconds, minutes, hours and/or days. For example, enough time may pass to allow any radioactive materials in the patient to reduce to less than 5% of their radiation level during 126. In some embodiments, new radioactive tracer material is injected for use during and/or after 142 (e.g., to allow for an up-to-date imaging of function).

At 144, the markers (e.g., from FIG. 1B) are identified in the acquired image, optionally automatically. Optionally, the identification is based on size, shape and/or location. Optionally or alternatively, a user indicates to the system (e.g., as described below) approximate locations of markers and/or specific identification of markers on the image.

At 146, the previously acquired data (e.g., NM data) is registered by aligning the marker indications in the data with the marker indications found in 144.

At 148 some or all of the NM data (or indications thereof, such as data segments or normalized NM data) and/or is optionally overlaid on the acquired image. Optionally, for example, using the methods described below, some of the acquired data is not shown.

At 150, an intervention is carried out using the combined image. Optionally, the imaging (e.g., 142) is used for tracking the location of a catheter or other interventional tool. Optionally or alternatively, such a catheter is detected using a position sensor and/or extracted from the image (142) and displayed to the user.

In some exemplary embodiments of the invention, the catheter is shown/located within the fused (hybrid image) that contains information from the different imaging modalities that are used. The catheter is navigated (e.g., using a navigation ability provided by the position sensor or by determining the position of the catheter within the image space). Optionally, the catheter is navigated toward a location that has certain functional information associated with the disease process, and such information is portrayed on the hybrid image at the time of the procedure and enables the interventionalist to navigate the catheter to such location. When reaching the location the interventionalist can perform a diagnostic step or a therapeutic step or both.

In some exemplary embodiments of the invention, registration is dynamic, for example, following changes in catheter position and/or changes in x-ray image (e.g., due to body motion and/or imager motion). Optionally, data processing (e.g., image matching and overlap is real-time, for example, within 20 seconds, 10 seconds, 5 seconds, 1 second, 0.5 seconds and/or intermediate times.

Exemplary NM Imaging System

Figure 2:
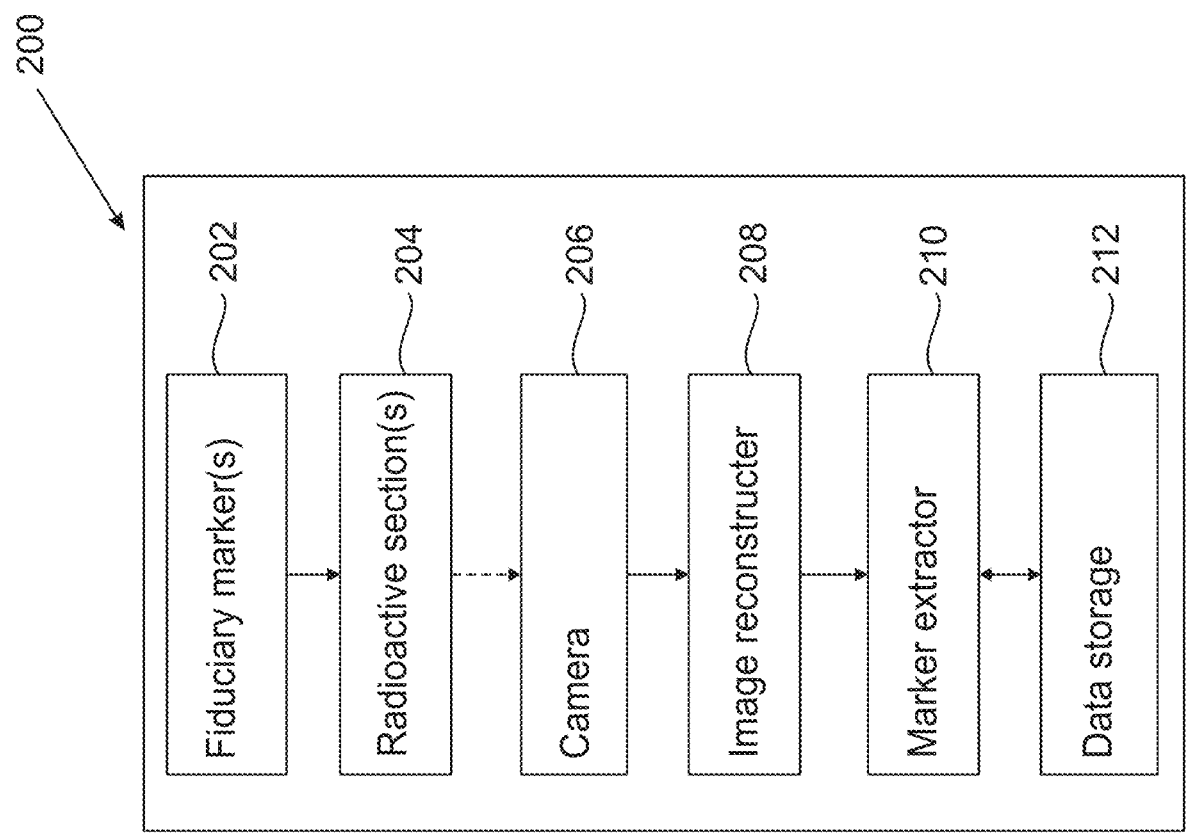
FIG. 2 is a block diagram of a system for nuclear medicine imaging, in accordance with some exemplary embodiments of the invention.

FIG. 2 is a block diagram of a system 200 for nuclear medicine imaging, which may be used for registering and/or otherwise combining NM data with x-ray data, in accordance with an exemplary embodiment of the invention, for example as described herein, for example, with respect to FIGS. 1A-1C.

System 200 includes one or more markers 202 (for example, between 2 and 6, for example, between 3 and 5) for attaching to a patient, optionally with a radio-opaque section, optionally a removable such section. Optionally, the tags are attachable to the body by screwing and/or adhesive.

In an exemplary embodiment of the invention, one or more radioactive tags/sections 204 are provided for attachment to marker(s) 202. In some embodiments, the tags are fluid. In some exemplary embodiments of the invention, the tags are encapsulated for easy attachment and/or removal. Optionally, attachment to the markers is by snap fitting (e.g., an interference mechanism). Optionally or alternatively, attachment is by screwing in and/or by opening and closing a latch.

A NM (nuclear medicine) camera 206 is optionally provided as part of the system, for example, a PET and/or a SPECT camera. In some embodiments of the invention, the camera is a cardiac imager, for example, D-Spect available from Biosensors International, Singapore.

An image reconstructer 208 is used to reconstruct a NM image using data provided by camera 206 and/or other sources. Exemplary reconstruction methods which may be used are described in PCT publication WO2014/115150, the disclosure of which is incorporated herein by reference.

A tag extractor 210 may be provided as a standalone element or as part of a general processor and is adapted to extract tag/marker positions from a NM image and/or data and/or from an x-ray image. Optionally, separate extractors are provided for NM data and for x-ray data (e.g., one or both being stand alone and/or associated with the data source on which they operate. Extractor 210 and/or a separate component may include a data combiner for combining NM data and x-ray data, for example, using methods described herein.

Data storage 212 is optionally provided and may store, for example, data, protocols, previous images, programs, authorization to apply one or more software components to data, log data and/or other patient and/or process related data.

Exemplary Navigation System

Figure 3:
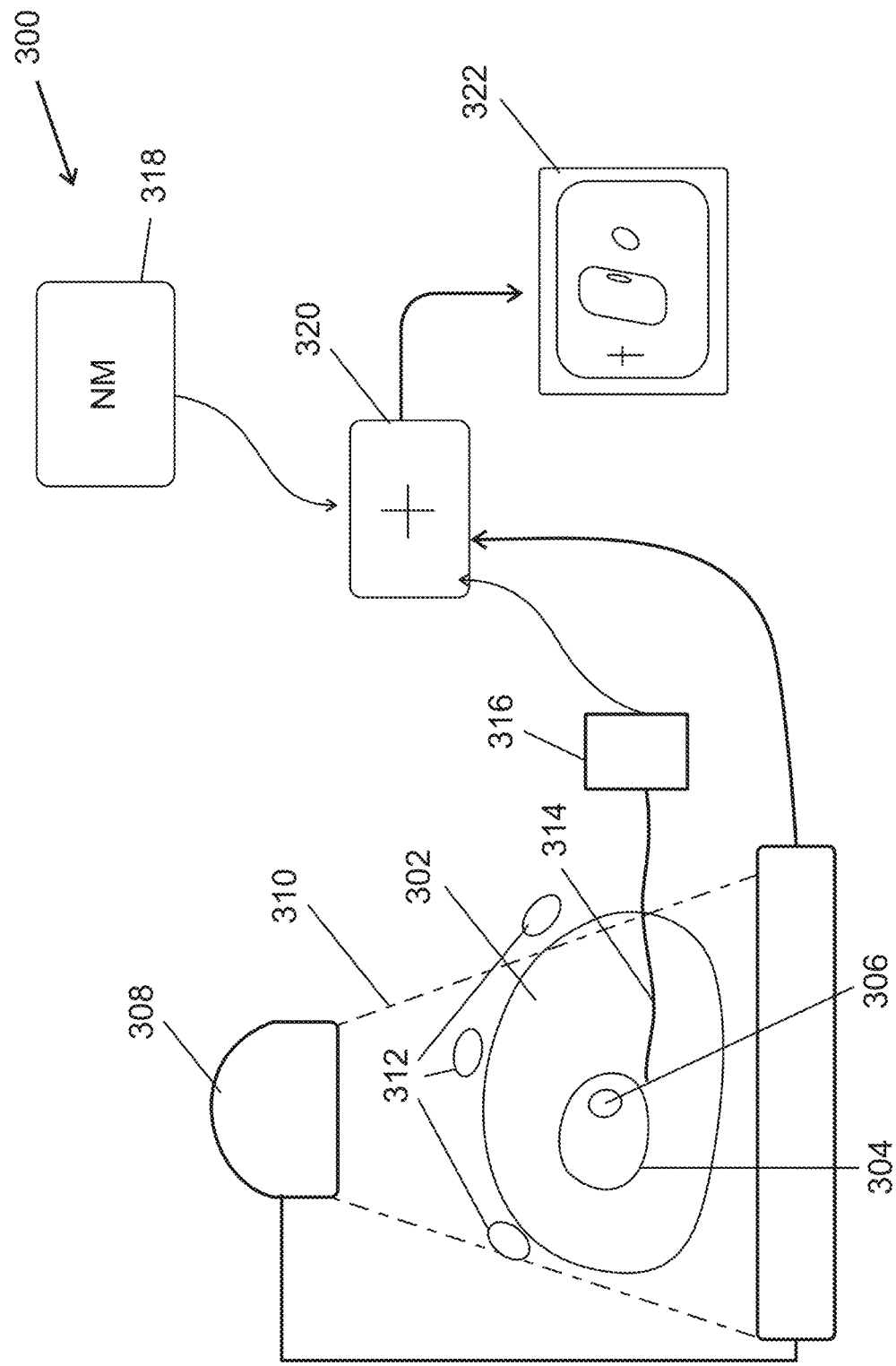
FIG. 3 is a block diagram of a system for intrabody navigation, in accordance with some exemplary embodiments of the invention.

FIG. 3 is a schematic block diagram of a system 100 for intrabody navigation and/or imaging, in accordance with an exemplary embodiment of the invention.

A patient 302 includes a heart (or other organ) 304 with a target 306 characterized by a radioactive emission when patient 302 is injected with a suitable radioactive marker. In some embodiments, the target is near and/or at a known positional relationship relative to the "hot spot" rather than thereat.

An optional x-ray imager 308 (e.g., a fluoroscope) acquires an image of patient 308 with a field of view (FOV) 310 and optionally one or more radio-opaque markers 312. As noted herein, markers 312 may also be radioactive. In an exemplary embodiment of the invention, FOV 310 is selected to be large enough to collect an image of the portions of interest and/or a navigation pathway to target 306. In an exemplary embodiment of the invention, FOV 310 is large enough to collect enough markers 112 to enable registration of the x-ray image to NM data, for example, as described herein.

In an exemplary embodiment of the invention, system 300 is used with a catheter 314. A position sensing system 316 may be used to determine the position of catheter 314 (e.g., a tip thereof) and/or of other parts of system 300, such as markers 312 (e.g., by touching a position sensor there to, or if they include a position sensor).

NM (Nuclear medicine) data 318 may be provided, for example, from storage and/or using a NM imager (not shown). Optionally, the NM imager is used while catheter 314 is inside patient 302. Optionally, the NM is reconstructed as an image. In other embodiments, an image is not reconstructed from the data before use of the catheter.

A processor 320 optionally analyses an acquired image from x-ray imager 308 for detecting markers 312 therein and optionally is used (e.g., as described below) to register the NM data to the catheter location and/or x-ray image. Optionally or alternatively, processor 320 combines NM data and x-ray data, for example, using Boolean logic or other rules, for example, as described below. Optionally or alternatively, for example, as described co-filed application attorney reference 59774, processor 320 reconstructs a NM image from NM data 318, using positions indicated by position sensing system 316, for example, the positions serving to indicate a constraint on where emissions are expected from. A display 322 optionally shows one or more of the combined image, a reconstructed NM image, catheter location and/or the image from imager 308.

In an exemplary embodiment of the invention, processor 320 tracks markers after they are first identified in the x-ray image. Optionally, the identification is manual or automatic, and the tracking is automatic, for example, using image tracking algorithms.

In some exemplary embodiments of the invention, processor 320 is a standalone device which may be connected (e.g., using data, video and/or computer peripheral connections) to an existing x-ray system (to obtain data and/or control acquisition), to an NM source (e.g., over a local and/or a wide area network) to receive data and/or control imaging, to a position sensing system (e.g., to obtain position data) and/or be connected to a dedicated or a standard display (e.g., a console of the x-ray system, position system and/or NM system) to display thereon. Optionally, the consul is also used to control processor 320).

Exemplary Fiduciary Marker

Figure 4:
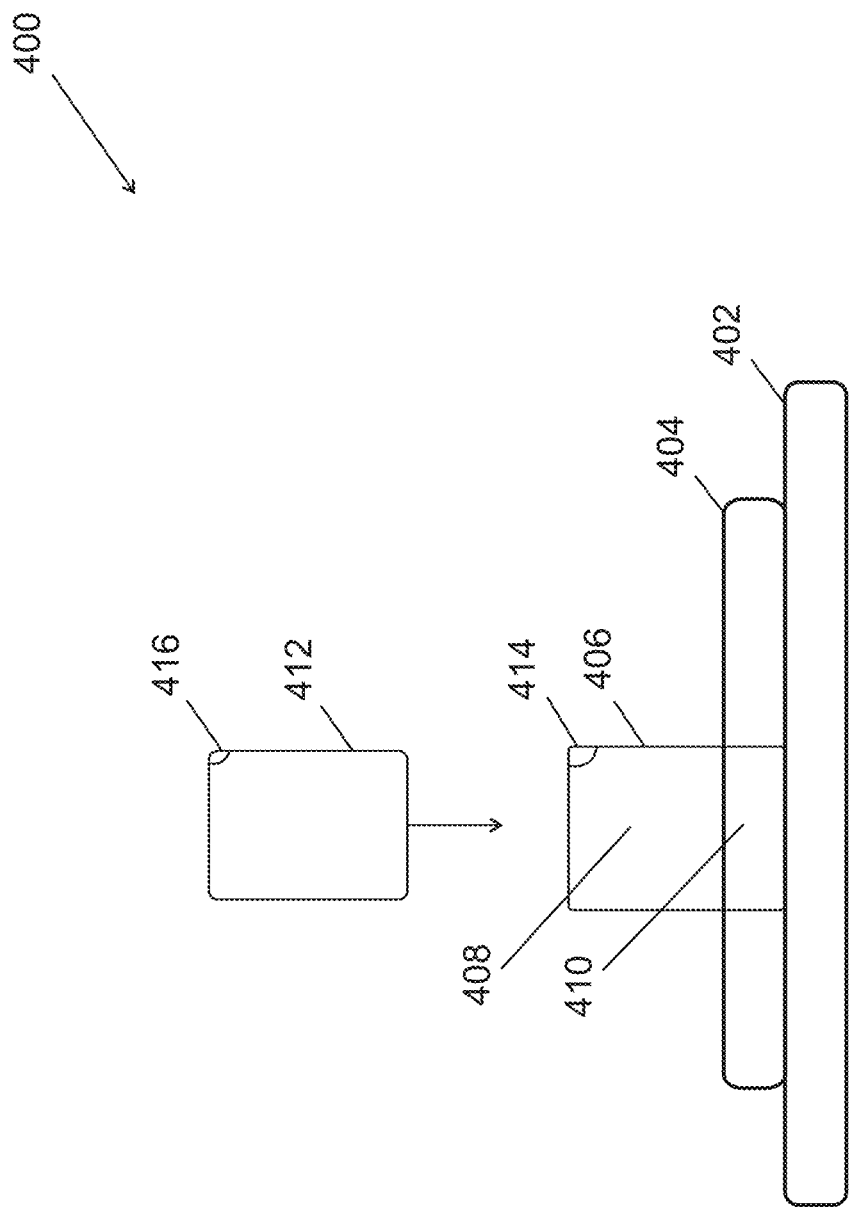
FIG. 4 is a schematic showing of a fiduciary marker, in accordance with some exemplary embodiments of the invention.

FIG. 4 is a schematic showing of a fiduciary marker 400 with a removable radioactive section 412, in accordance with some exemplary embodiments of the invention. In an exemplary embodiment of the invention, marker 400 is used as one or all of markers 312 as described with reference to FIGS. 1A-3.

A radio-opaque section 404 is attachable to a body using an adhesive layer 402, for example, of a type known n the art. In some exemplary embodiments of the invention, section 404 is patterned so that it can be recognized in an x-ray image and/or be used for registration. Optionally, the patterning defines a central location 410, which is optionally aligned in 2D or 3D with section 412 and can be identified accurately in x-ray images. Optionally or alternatively, patterning provides an indication of the orientation of marker 400. For example, if the section 404 defines concentric circles, the circles appear as ellipses when seen in the x-ray image, if marker 400 is not in a plane perpendicular to FOV 310. Optionally or alternatively, markings are used to better extract the size of the marker, its (rotational) orientation and/or its distance (e.g., including a series of gaps of different and known sizes, for analysis after imaging.

Optionally or alternatively, to an adhesive layer for attachment, a separate adhesive section (e.g., with double sided adhesion) may be used. Optionally or alternatively, attachment may be via surgical clips or sutures and/or screws (e.g., to bone). Marker 400 may include one or more apertures, recesses and/or protrusions to support such attachment mechanism.

In some exemplary embodiments of the invention, marker 400 includes a connector 406 for attaching to section 412. Optionally, connector 406 includes a recess 408 for receiving section 412. Alternative attachment mechanism, such as a latch and/or an adhesive or other temporary connection layer (such as a hook and loop-type connector) may be used as well. In some exemplary embodiments of the invention, connector 406 includes an interference element 414 which interlocks and/or blocks movement of a matching element 416 in section 412. Optionally, element 414 comprises a projection and element 416 comprises a matching recess, or vice versa. Optionally, the attachment of section 412 to connector 406 does not prevent relative rotation therebetween. In some embodiments, such rotation is prevented.

In some embodiments, section 412 is for a different type of functional imaging, such as MRI or ultrasound. Optionally or alternatively, section 404 is replaced by a marker for a different type of imaging than x-ray, for example, MRI or ultrasound.

In some embodiments of the invention, marker 400 comprises a position sensor, for example in addition to or instead of radio-opaque section 404. Optionally, one or more indications on section 404 are used for exactly receiving a position sensing stylus (or catheter) during position calibration thereof.

Marker 400 is described as being useful for attaching to body surfaces. Optionally, the surface is the skin. Optionally or alternatively, other surfaces, such as mucus surfaces and/or surfaces inside the body are used for attachment. Optionally, inside the body, marker 400 is made more streamlined and/or flat than shown. Optionally or alternatively, markers for use inside the body are in the shape of an ellipsoid and attached using a screw mechanism.

In some exemplary embodiments of the invention, a skin marker has a maximum extent of less than 40 mm, 30 mm, 20 mm, 10 mm, 5 mm or intermediate sizes. Optionally, the height of the marker (way from the skin) is less than 20 mm, 10 mm, 5 mm. In an exemplary embodiment of the invention, the radio-opaque portion of the marker has an area (projected on the skin) of less than 4 cm^2, 2 cm^2, 1 cm^2, 20 mm^2 or intermediate areas.

In some exemplary embodiments of the invention, an implantable marker has a maximum extent of less than 30 mm, 20 mm, 10 mm or intermediate extents. Optionally or alternatively, the marker is generally cylindrical and has a diameter of less than 10 mm, 5 mm, 3 mm, 1 mm or intermediate diameter sizes.

In an exemplary embodiment of the invention, for either marker type the NM section has a volume of less than 10 cm^3, 5 cm^3, 1 cm^3, 0.5 cm^3, 0.1 cm^3 or intermediate sizes. Optionally, the section includes a capsulation part, for example, of a thickness of between 0.1 and 1 mm and an inner volume. Optionally, the encapsulating part includes a valve, or other openable section, such as a self-sealing elastic section for material ingress.

In some embodiments of the invention, the amount of radiation in the marker is larger than used in the body, because the radioactive section is removable. For example, the amount of radiation can be 1 mC, 10 mC, 100 mC or intermediate or smaller or larger amounts. In some embodiments a standard tracer is used in the marker.

In some exemplary embodiments of the invention, as the marker has a well defines shaped, an unknown amount of radiation is used (for example, an expired medical dose) and the marker is detected based on shape/geometry and/or position with the amount of signal being less important for detection (in standard imaging, the amount of signal is often the main feature used for diagnosis).

Exemplary Composite Display

Figure 5:
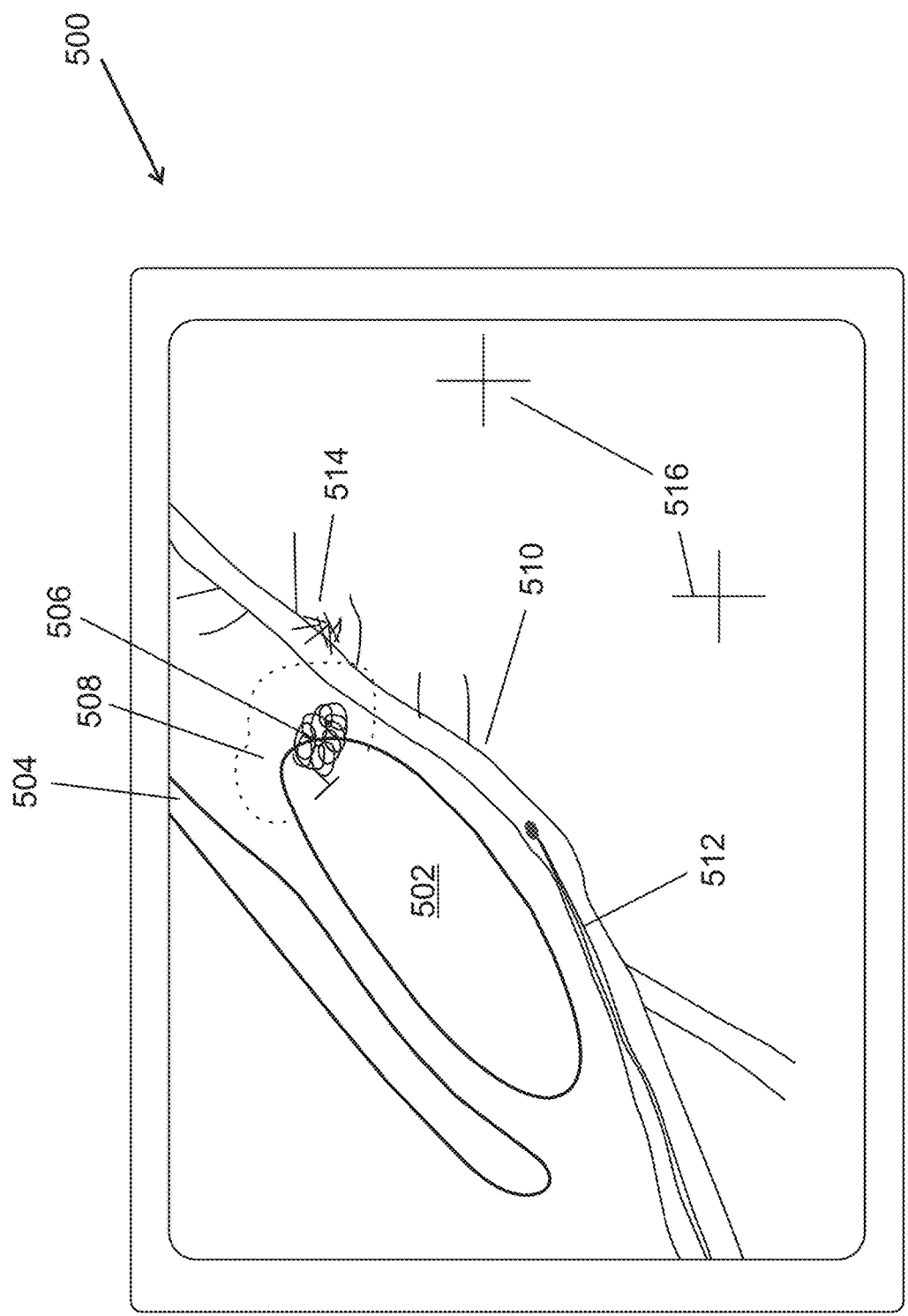
FIG. 5 is a schematic display showing a body, NM-derived data and navigational-aide data, in accordance with some exemplary embodiments of the invention.

FIG. 5 is a schematic display 500 showing a body, NM-derived data and navigational-aide data, generated by processor 320, for example, in accordance with some exemplary embodiments of the invention. In particular, display 500 shows a combination of NM data, x-ray data and/or a tool.

Reference 502 shows a target organ/tissue with nearby tissue 504, such as a bone. Reference 506 indicates a hotspot in NM data and reference 508 indicates a structural outline (e.g., the edge of tissue 502) which generally coincides with hotspot 506 For example, hot spot 506 can be a tumor as visualized using an FDG tracer in PET imaging. In some cases the functional image does not match the structural image exactly (for example, as shown) this may be the result of tissue changes not showing in the structural image.

Reference 510 shows a blood vessel, within which a catheter 512 is traveling. The image of catheter 512 may be, for example, extracted from the x-ray image, copied there-from and/or reconstructed, for example, using positioning data about the catheter an structural limitation imposed by vessel 510.

Reference 514 indicates an additional (or alternative) hotspot from the NM data.

References 516 indicate fiduciary marker images from the x-ray image, which are optionally removed from the image, or, as here, kept in the image and/or indicated synthetically.

Exemplary Position Estimation

Figure 6:
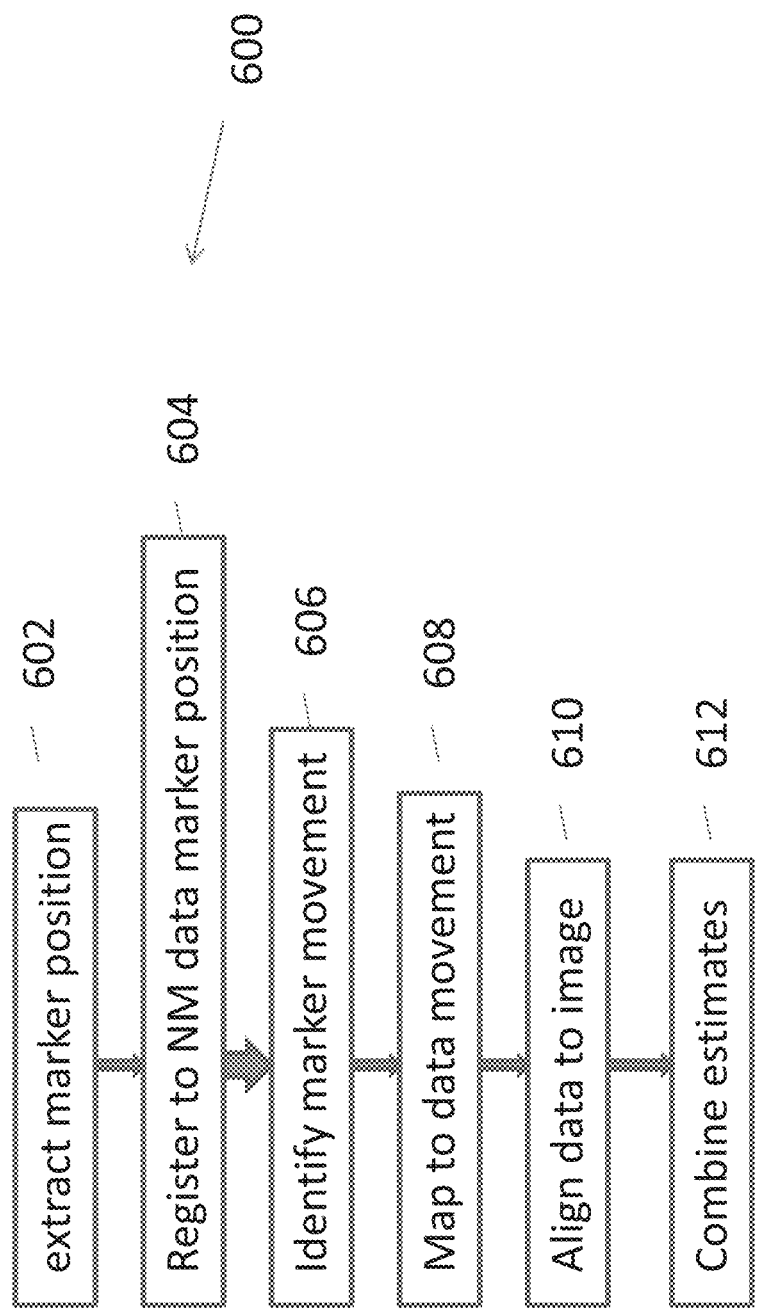
FIG. 6 is a flowchart of a method of position estimation, in accordance with some exemplary embodiments of the invention.

FIG. 6 is a flowchart 600 of a method of position estimation, in accordance with an exemplary embodiment of the invention. As can be noted marker position in NM data and x-ray data may not match up exactly. Further, patient motion during NM imaging and/or x-ray imaging may affect such alignment. Finally, NM data may be 3D, while x-ray data may be 2D.

At 602, marker position is extracted from the x-ray image. This may be repeated, for example, according to patient movement detection in the image and/or periodically. It is noted that the x-ray image may be moved during the procedure, for example by translating and/or rotating the imager. Optionally, the system indicates to a user if FOV 310 does not include sufficient markers for image alignment. Optionally or alternatively, a position sensor is mounted on the x-ray imager so that once aligned with the NM data coordinates, further movements can be tracked using the position sensors and bypassing, if desired, the use of markers.

At 604 the extracted position is registered to NM marker position. It is noted that such mapping may be based, for example, on individual identification of the markers, for example, based on shape (in x-ray and/or NM image) and energy (NM image. Optionally, registration is based on a projection of the NM data to the x-ray plane and then determining a 2D mapping between the identified corresponding markers.

At 606, movement of the markers is identified (e.g., due to breathing, heartbeat, GI peristaltic). Optionally, identification is by automatic image comparison and/or by tracking the position of the markers and/or relative position thereof over time.

At 608, the NM data is deformed according to the detected movement of one or more markers. Optionally, deforming is by generating a deforming transformation between the markers and applying that transformation when mapping and/or displaying.

At 610, the deformation is applied and the NM data is aligned to the x-ray image.

At 612, optionally, note is taken of the existence of a plurality of NM marker positions (e.g., corresponding to different parts of a movement cycle). Optionally, a best fit (e.g., using a metric of least non-linear deformation) between marker positions in the two modalities is determined.

Optionally, the actual alignment of NM data and x-ray data includes a weighted or other combination of estimates, for example, based on alignment of markers, range of motions of markers, position of the catheter and/or other position sensing system input.

Data Combining, for Example for Screening

Figure 7:
FIG. 7 is a flowchart of a method of data combining, in accordance with some exemplary embodiments of the invention.

FIG. 7 is a flowchart of a method 700 of data combining of two images (e.g., functional and structural), in accordance with an exemplary embodiment of the invention. A display showing both NM data and x-ray data may be so visually crowded as to have a reduced utility. In an exemplary embodiment of the invention, one or more rules are applied so as to avoid displaying (apparently) unneeded information.

In some exemplary embodiments of the invention, the rules are applied after segmentation and/or object recognition in one or both images. Optionally or alternatively, the rules are applied on pixel-level data. In some embodiments, a rule relates to pixel level data in one image and objects in another. In some exemplary embodiments of the invention, actual objects are not identified. Rather, features representing groups of pixels are used as a basis for rules.

At 702, a first image (e.g., a NM image, such as an FDG image) is provided. This image may be, for example, a 2D image, a 3D image or a 4D (time+3D) image. The image optionally includes indications of multiple tracers. In some cases, data, rather than an image is provided. The data may be arranged using a spatial index.

At 704 a second image (e.g., x-ray) or data set is provided.

At 706 the two images are aligned so that data in one image can be corresponded with data in the other image.

At 708, a mapping (e.g., a projection) from one image or data set to the other is generated, for example, based on the determined alignment.

At 710, one or more rules for display are applied to one or both images.

At 712 a display is generated based on the two images and the rules. Optionally, the display comprises one image with parts of the other imager overlaid and/or replacing parts thereof. Optionally or alternatively, the display uses layers. Optionally or alternatively, the display includes parts of one image and parts of the other image. Optionally or alternatively, what is displayed is not images by rather a synthetic image based on data. For example, temperature data may be displayed as isothermal lines.

In some embodiments of the invention, rules feedback to image generation. For example, structural features in an x-ray image may be used to constrain reconstruction of a NM image from the NM data. For example, the NM data is reconstructed (e.g., reprojected) using information from the structural image as constraints. In another example, structural image information is used to define areas of interest for further processing of the NM data. For example, hot spots of a certain size and/or shape (e.g., ganglions) may be searched for within a geometry defined by the structure.

In a particular example, metastases are highlighted by the following application of one or more of the following rules. A first rule (applied to the NM image) is identifying all FDG hotspots larger than 6 mm in diameter. A second rule (applied to the x-ray image) is identifying locations within 1 cm (or 2 cm) from a vessel of diameter greater than 3 mm (e.g., locations treatable using a catheter, for a catheter based procedure). A third rule (applied to the two images in combination) is selecting for display overlaying the x-ray image, only those hotspots in the NM image which fall in the set of locations of the x-ray image. As illustrated a rule may be applied to images, to segments and/or objects in the image and/or between two images and/or objects or results of rule applications.

For example, a rule may define a size or a shape of an object. Optionally or alternatively, a rule may define a distance between objects. Optionally or alternatively, a rule may define an amplitude of an object. Optionally or alternatively, a rule may define a statistic of an object, such as relative to other objects (e.g., standard deviation in difference. Optionally or alternatively, a rule may define a spatial pattern (e.g., tissue near bone). Optionally or alternatively, a rule may define an object relative to other objects. Optionally or alternatively, a rule may define a contrast within an object or between one object and another. Optionally or alternatively, a rule may import additional data, such as electrophysiological data and/or surrounding tissue type (e.g., from a CT number of a CT image).

Figure 8:
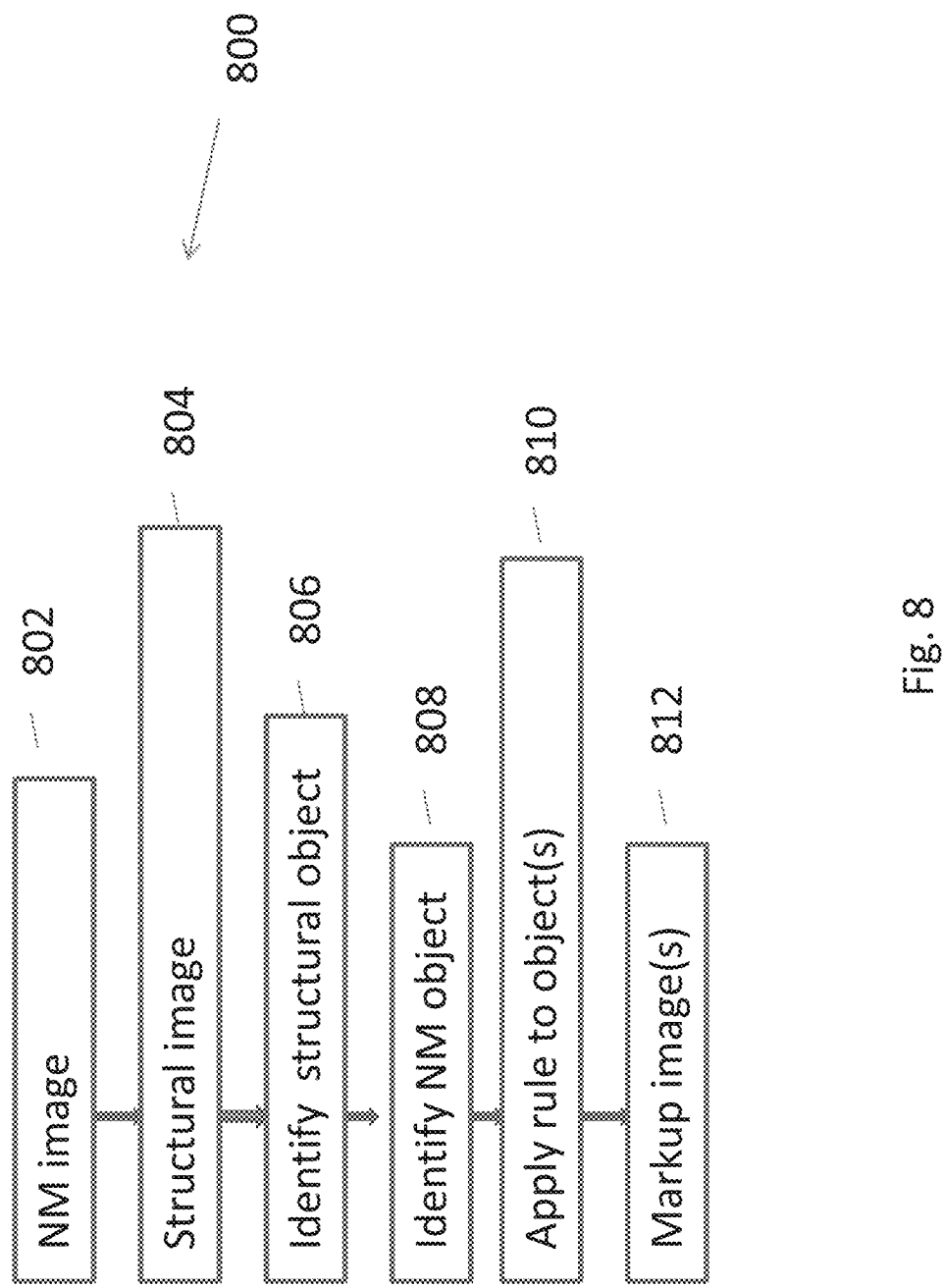
FIG. 8 is a flowchart of a method of screening patients for cancer treatment, in accordance with some exemplary embodiments of the invention.

FIG. 8 is a flowchart of a method 800 of screening patients for cancer treatment, in accordance with an exemplary embodiment of the invention.

At 802 a NM image of a patient is acquired.

At 804 a structural image (e.g., x-ray) is acquired.

At 806, a potentially cancerous object is identified n the x-ray image.

At 808 a potentially cancerous object is identified n the NM image.

At 810, one or more rules are applied to the identified objects.

At 812 an image is generated.

Figure 9:
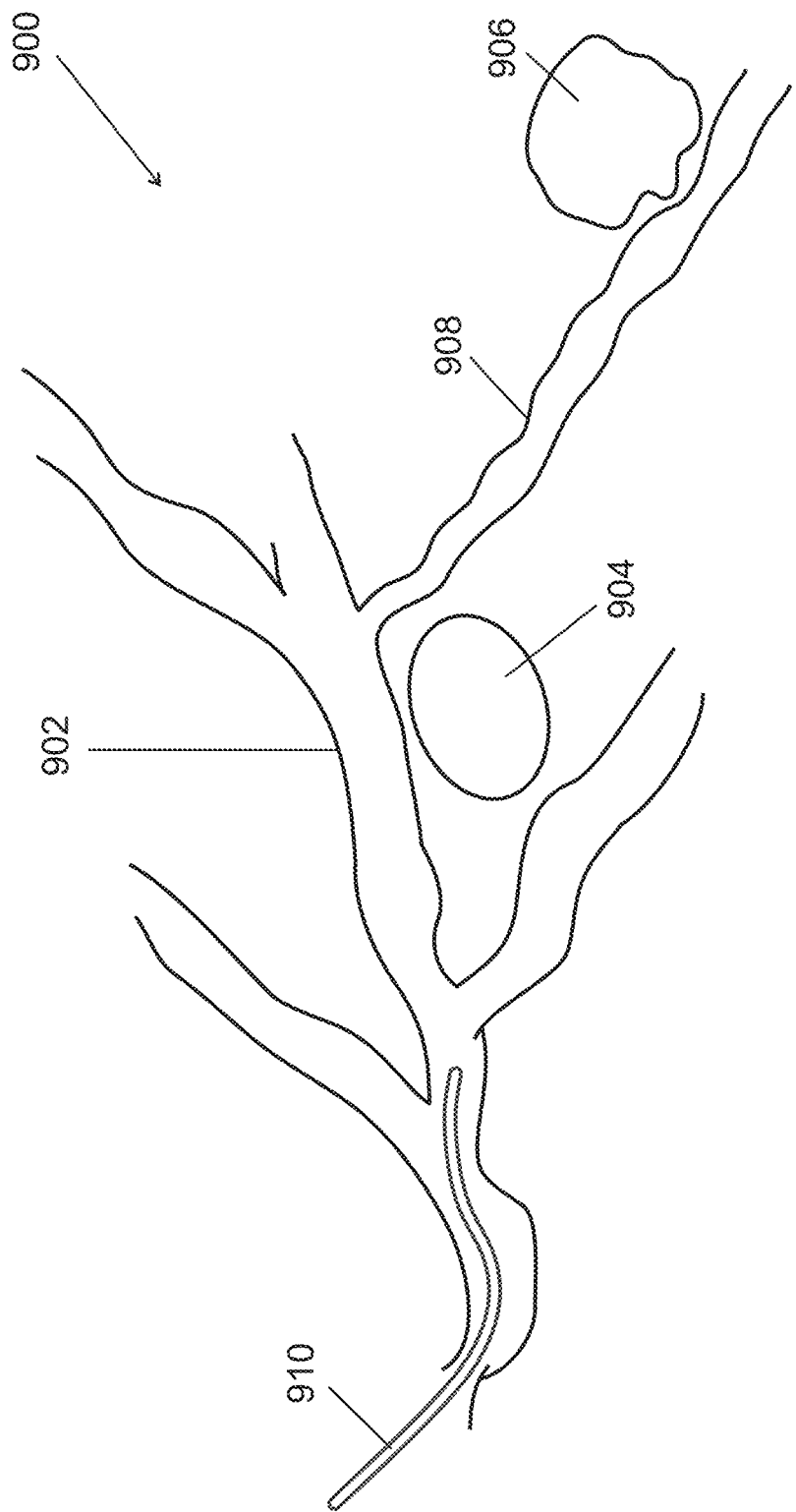
FIG. 9 is a schematic display showing combined data and an optional treatment device, in accordance with some exemplary embodiments of the invention.

FIG. 9 is a schematic display 900 showing combined data and an optional treatment device, in accordance with an exemplary embodiment of the invention. In an exemplary embodiment of the invention, the above rules are applied during a treatment session, for example, using a catheter 910.

Reference 902 indicates a large vessel in a vascular tree identified in the x-ray image. Reference 904 is a potentially cancerous object displayed because it meets the rules described with reference to FIG. 8 (large and also near a large vessel). Reference 906 may also be cancerous but is optionally not shown (or indicated as to be ignored) as it is near a too-small vessel 908 and not near a large enough vessel 902. Catheter 910 optionally includes a position sensor and is guided on the image shown in FIG. 9. In an exemplary embodiment of the invention, after rule application the following data is transmitted to the positioning system: the locations of vessels through which the catheter can traverse; locations and sizes of tumors to be treated; and/or treatment parameters and/or expected results; the data may be projected to 2D space.

Exemplary Alternative Fiduciary Markers

Figure 10A:
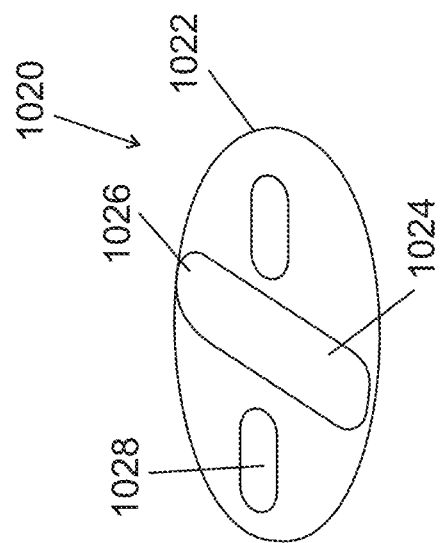
FIGS. 10A-10C are showings of exemplary fiduciary markers, in accordance with some exemplary embodiments of the invention.
Figure 10B:
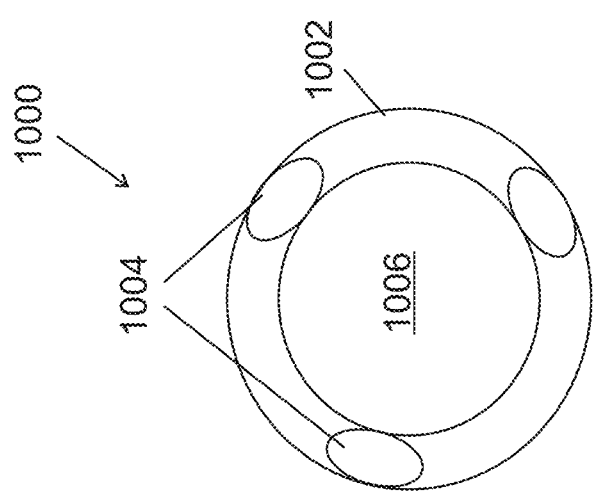
Figure 10C:
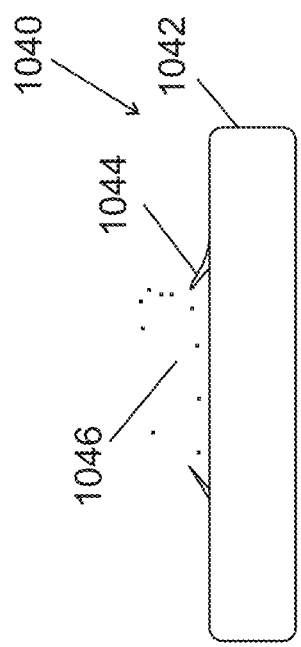

FIGS. 10A-10C are showings of exemplary fiduciary markers, in accordance with some exemplary embodiments of the invention. In some implementations, the geometric centers of the radio-opaque and of the radio-active sections are made to coincide in 2D or 3D (optionally when weighted for amount of opacity or activity, in a manner analogous to center of gravity).

In an exemplary embodiment of the invention, the markers do not have overlapping sections of radioactive and radio-opaque material, or overlap in direction of x-ray imaging is less than 50%, 30%, 20% or intermediate percentages of the cross-section area of the radioactive material (in this direction). This may reduce blockage of radioactive signal by the radio-opaque portions of the marker.

FIG. 10A shows a ring shaped fiduciary marker in which radioactive and radio-opaque section share a center. Shapes other than rings may be used as well. In this figure, a marker 1000 includes a ring 1002 with a plurality of radio-opaque sections 1004 and a central aperture 1006. In some embodiments, ring 1002 is hollow and a radioactive material can be injected (if fluid) or inserted (if solid or encapsulated) thereinto, via an opening (not shown, for example, at 1004). In alternative embodiments, ring 1002 is radio-opaque and sections 1004 are (optionally removable) radio-active sections. Optionally, sections 1004 are attached to ring 1002 using a connector or using an adhesive layer, for example, as described above with respect to FIG. 4.

FIG. 10B shows a marker 1020 suitable for insertion into the body, in accordance with an exemplary embodiment of the invention. While shown in cross-section, marker 1020 can be ellipsoid in shape. Optionally, marker 1020 includes a curved metal or polymer portions, such as a helix or a screw, for anchoring.

In the example shown, a polymer body 1022 includes one or more, optionally two radio-opaque sections 1028 which have a center of gravity coinciding with the center of gravity of a recess 1026 for a radio-active section.

FIG. 10C shows a side cross-sectional view of flat marker 1040 including a plurality of projections 1044 on base 1042 (optionally radio-opaque at least in part) and adapted to receive in a region 1046 therebetween a radioactive section. Optionally, projections 1044 are radio-opaque. It should be noted that the centers of activity of the radio-opaque section and the radio-active section optionally coincide only when viewed from above, but not from the side.

Figure 11A:
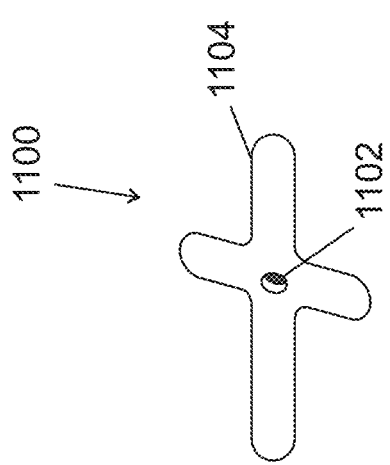
FIGS. 11A-11C are showings of exemplary removable radioactive tags, in accordance with some exemplary embodiments of the invention.
Figure 11B:
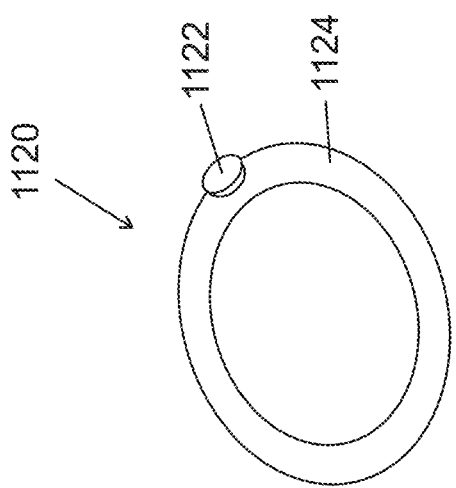
Figure 11C:
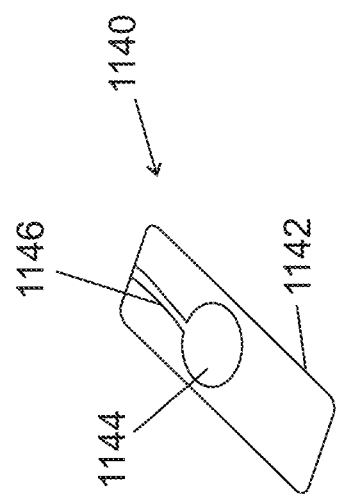

FIGS. 11A-11C are showings of exemplary removable radioactive tags, in accordance with some exemplary embodiments of the invention, specifically indicating some possibilities of asymmetry. In some exemplary embodiments of the invention, software in extractor 320 and/or other image processing parts of system 300 is programmed to automatically recognize the asymmetry and correct for it and/or include an input for receiving an identification of the markers and/or their properties so asymmetry can be utilized and/or corrected for.

In some embodiments, the asymmetry is between a "naturally" indicated center of radio-opacity and a "natural" indicated center of radio-activity. For example, a point where two radio-opaque sections (or their virtual lines) intersect, may be different from a center of radiation of the radio-active section or from an indicated center (e.g., center of rotation) thereof.

FIG. 11A shows a cross-shaped (or other shape with arms) tag 1100, with a well defined center and a radio-active marker 1102 at said center. Optionally, tag 1100 has different length arms (e.g., differing by more than a factor of 1:1.5 or 1:2), for example, to help determine orientation from an x-ray image.

FIG. 11B shows a different type of asymmetry in a marker 1120, in which a ring 1124 is radio-opaque, but a radio-section 1122 is not symmetrically arranged. Optionally, the location of section 1122 can be identified in the x-ray image, for example, using its different size and/or shape and/or opacity. As in other embodiments, the functions of radioactivity and radio-opacity may be switched. Also, it is noted that some radio-active sections are themselves radio-opaque.

FIG. 11C shows a cross-sectional view of a marker 1140, optionally implantable, including body 1142 which may be radio-opaque or may be attached to a radio-opaque marker. A volume 1144 is set up to receive a radio-active fluid via an optional channel 1146, optionally a self-sealing channel, for example, including a silicon valve or a rubber plug. In use, radioactive fluid is injected into volume 1144 by inserting a needle at least partway into channel 1146 and injecting the fluid via the needle. Optionally, when radioactive imaging is completed, a needle is inserted into channel 1146 and/or volume 1144 and the fluid sucked out. Optionally, marker body 1142 is elastic and can compress when volume 1144 is emptied.

Such a mechanism for injection of fluid may be used with other markers, for example, marker 1120 can have a channel formed therein along all or part of its circumference for receiving a radioactive fluid.

In some embodiments of the invention, volume 1144 is not symmetrically spaced with respect to the shape of marker 1142 and/or its radio opacity.

In some embodiments of the invention, radio-opaque markers are marked to indicate their asymmetry with respect to radio-active sections thereof. Optionally, software in system 300 reads and/or otherwise identifies such markings so as to correctly align NM coordinates and x-ray coordinates, for example, using an offset in space based on the markings.

In some embodiments of the invention, high resolution NM imaging is needed, for example, if a marker is in the form of an arc and/or unevenly arranged along the circumference of a circle, low resolution imaging may indicate a point source not at the center of rotation of the arc. High resolution imaging can identify the shape of the arc/circle and thus identify the correct center thereof. Similarly, high resolution imaging and/or suitable software, may be required for other geometric shapes where the geometric center of the shape or an indicated center (center of a star) does not coincide with the center (average) location of radio-activity.

In some embodiments of the invention, radioactive sections of a marker use multiple energies (e.g., possibly as different sections, each one with a different emission energy) and/or a mixture of energies in one section and/or energies different from those used in a body in general or for a specific treatment. Such use of different energies may assist in distinguishing the radio-active marker from emissions from the body. Optionally or alternatively, the shape of the marker (e.g., and/or sharp geometric boundaries) is used for such distinguishing.

It is expected that during the life of a patent maturing from this application many relevant markers will be developed and the scope of the term marker is intended to include all such new technologies a priori.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A fiduciary marker comprising:
    a hollow body comprising:
        (a) a radio-opaque section; and
        (b) a radioactive marking section comprising a mounting for a removable radio-active marker portion
            wherein said radioactive marking section has a center activity of radiation co-located in at least two dimensions with a center of opacity of said radio-opaque section;
    wherein said radio-opaque section and said radioactive marking section are arranged to define between them an unoccupied hollow in the fiduciary marker.

2. A fiduciary marker according to claim 1, wherein said mounting comprises a receptacle for a radioactive fluid.

3. A fiduciary marker according to claim 1, wherein said mounting comprises a receptacle for a radioactive insert.

4. A fiduciary marker according to claim 1, wherein said mounting comprises an interference based fitting.

5. A fiduciary marker according to claim 1, wherein at least one of said sections is ring-shaped.

6. A fiduciary marker according to claim 1, comprising an adhesive layer with adhesive suitable for long-term adhesion to a human skin.

7. A fiduciary marker according to claim 1, comprising a radioactive marking portion mounted in said mounting.

8. A fiduciary marker according to claim 7, wherein an energy signature of said radioactive portion includes a plurality of distinct energy bands.

9. A fiduciary marker according to claim 8, wherein at least one of said energy bands is different from energy bands of any one of I-123 and Tc-99.

10. A fiduciary marker according to claim 8, wherein at least one of said energy bands is different from energy bands of an energy signature of a biocompatible tracer in clinical use.

11. A fiduciary marker according to claim 7, wherein said radioactive marker portion is formed of a non-bio-compatible radioactive material.

12. A fiduciary marker according to claim 1, wherein:
(a) the radio-opaque section defines at least one point for identification in an x-ray image; and
(b) the radioactive marking section defines at least one point for identification in a Nuclear Medicine image,
wherein said two points are co-located and overlap in at least two dimensions.

13. A marker according to claim 12, wherein at least one of said points is defined by a portion of said fiduciary marker.

14. A fiduciary marker according to claim 1, wherein the radioactive marker section comprises a hollow ring having a hollow interior and surrounding a central aperture; wherein the hollow interior is configured to receive the removable radio-active marker portion.

15. A fiduciary marker according to claim 1, wherein one or more of:
said radioactive marker section is divided into a plurality of sub-sections separately connected to said radio-opaque section; and
said radio-opaque section is divided into a plurality of sub-sections separately connected to said radioactive marker section.

16. A fiduciary marker according to claim 1, wherein at least one of the radioactive marker section and the radio-opaque section comprises a ring, and the other of the sections is not symmetrically arranged relative to a center of the ring.

17. A fiduciary marker according to claim 1, wherein the radio-opaque section comprises a plurality of arms extending from a center comprising the radioactive marking section.

18. A fiduciary marker according to claim 1, wherein the radioactive marking section comprises a lumen configured to receive radio-active fluid via a self-sealing channel.

19. A fiduciary marker according to claim 18, wherein the self-sealing channel is configured to self seal after receiving fluid injected through it by a needle.

20. A fiduciary marker according to claim 1, wherein the radio-opaque section comprises a plurality of projections projecting into a central region, and adapted to receive within the central region the radio-active marker portion.

21. A fiduciary marker comprising:
(a) a radio-opaque section; and
(b) a radioactive marking section comprising a mounting for a removable radioactive marker portion;
wherein at least one of the radioactive marker section and the radio-opaque section comprises a ring, and the other of the sections is not symmetrically arranged relative to a center of the ring.

22. The fiduciary marker according to claim 21, wherein said ring has a hollow interior configured to receive the removable radioactive marker portion.

23. The fiduciary marker according to claim 21, wherein said radio-opaque section defines at least one point for identification in an x-ray image, the radioactive marking section defines at least one point for identification in a Nuclear Medicine image, where said two points are co-located and overlap in at least two dimensions.

24. The fiduciary marker according to claim 21, wherein said radioactive marking section has a center activity of radiation co-located in at least two dimensions with a center of opacity of said radio-opaque section.

25. The fiduciary marker according to claim 21, wherein said mounting includes a feature from the group consisting of:
a receptacle for a radioactive fluid;
a receptacle for a radioactive insert;
an interference based fitting.

26. The fiduciary marker according to claim 21, wherein said radio-opaque section is divided into a plurality of sub-sections separately connected to said radioactive marker section.

27. The fiduciary marker according to claim 21, wherein said radioactive marking section includes a feature from the group consisting of:
said radioactive marker portion has an energy signature which includes a plurality of distinct energy bands;
said radioactive marker portion is formed of a non-biocompatible radioactive material
said radioactive marking section comprises a lumen configured to receive radio-active fluid via a self-sealing channel.

28. The fiduciary marker according to claim 21, wherein said fiduciary marker comprises an adhesive layer with adhesive suitable for long-term adhesion to a human skin.

29. A fiduciary marker comprising:
(a) a radio-opaque section; and
(b) a radioactive marking section comprising a mounting for a removable radio-active marker portion;
wherein the radio-opaque section comprises a plurality of arms extending from a center comprising the radioactive marking section.

30. The fiduciary marker according to claim 29, wherein said radio-opaque section defines at least one point for identification in an x-ray image, the radioactive marking section defines at least one point for identification in a Nuclear Medicine image, where said two points are co-located and overlap in at least two dimensions.

31. The fiduciary marker according to claim 29, wherein said radioactive marking section has a center activity of radiation co-located in at least two dimensions with a center of opacity of said radio-opaque section.

32. The fiduciary marker according to claim 29, wherein said mounting includes a feature from the group consisting of:
a receptacle for a radioactive fluid;
a receptacle for a radioactive insert;
an interference based fitting.

33. The fiduciary marker according to claim 29, wherein said radio-opaque section is divided into a plurality of sub-sections separately connected to said radioactive marker section.

34. The fiduciary marker according to claim 29, wherein said radioactive marking section includes a feature from the group consisting of:
- said radioactive marker portion has an energy signature which includes a plurality of distinct energy bands;
- said radioactive marker portion is formed of a non-biocompatible radioactive material
- said radioactive marking section comprises a lumen configured to receive radio-active fluid via a self-sealing channel.

35. The fiduciary marker according to claim 29, wherein said fiduciary marker comprises an adhesive layer with adhesive suitable for long-term adhesion to a human skin.

\* \* \* \* \*